(12) United States Patent
Romero Filardo et al.

(10) Patent No.: US 12,704,502 B2
(45) Date of Patent: Aug. 11, 2026

(54) METHODS AND SYSTEMS FOR DETERMINING METABOLIC POISE AND CAPACITY OF LIVING CELLS

(71) Applicant: AGILENT TECHNOLOGIES, INC., Santa Clara, CA (US)

(72) Inventors: Maria Natalia Romero Filardo, Brookline, MA (US); James Niall Hynes, Little Island (IE)

(73) Assignee: AGILENT TECHNOLOGIES, INC., Santa Clara, CA (US)

(*) Notice: Subject to any disclaimer, the term of this patent is extended or adjusted under 35 U.S.C. 154(b) by 828 days.

(21) Appl. No.: 18/045,607

(22) Filed: Oct. 11, 2022

(65) Prior Publication Data

US 2023/0128888 A1 Apr. 27, 2023

Related U.S. Application Data

(60) Provisional application No. 63/254,927, filed on Oct. 12, 2021.

(51) Int. Cl.
*G01N 33/50* (2006.01)

(52) U.S. Cl.
CPC ................................ *G01N 33/5038* (2013.01)

(58) Field of Classification Search
CPC .... A61K 47/60; A61K 47/551; A61K 31/495; G01N 33/5038
See application file for complete search history.

(56) References Cited

U.S. PATENT DOCUMENTS

2016/0281049 A1 9/2016 Ferrick et al.
2018/0360975 A1* 12/2018 Levin .................... A61K 47/60

OTHER PUBLICATIONS

Anon et al., "Report Generator User Guide Agilent Seahorse XF Cell Mito Stress Test" Agilent (2020), XP93012595.
Fenninger et al., "P38 Bioenergetic Profile of Isolated Human Peripheral Lymphocytes" Human Immunology (2019) vol. 180, XP085768125.
Van Der Windt Gerritje et al., "Measuring Bioenergetics in T Cells Using a Seahorse Extracellular Flux Analyzer" Nanoscience (2016) vol. 5, No. 1, XP93012601.
Tan et al., "The Profiles of Mitochondrial Respiration and Glycolysis Using Extracellular Flux Analysis in Porcine Enterocyte IPEC-J2" Animal Nutrition (2015) vol. 1, No. 3, pp. 239-243, XP93012574.
Radde et al., "Nuclear Respiratory Factor-1 and Bioenergetics in Tamoxifen-resistant Breast Cancer Cells" Experimental Cell Research (2016) vol. 347, No. 1 pp. 222-231 XP029708602.
Ravi et al., "Defining the Effects of Storage on Platelet Bioenergetics: The Role of Increased Proton Leak" Biochimica Et Biophysica Acta. Molecular Basis of Disease (2015) vol. 1852, No. 11, pp. 2525-2534 XP029277090.
Kenwood et al., "Identification of a Novel Mitochondrial Uncoupler that does not Depolarize the Plasma Membrane" Molecular Metabolism (2015) vol. 3, No. 2, pp. 114-123 XP055414206.
Anon et al., "Functional Mitochondrial Toxicity Assay" Cyprotex in Vitro Toxicology (2021) XP93012588.
International Search Report and Written Opinion for International Application No. PCT/US2022/077884 dated Jan. 20, 2023.

* cited by examiner

*Primary Examiner* — Lam S Nguyen

(57) ABSTRACT

Disclosed herein are methods and systems for evaluating the bioenergetic poise and bioenergetic capacity of living cells in a single assay.

22 Claims, 22 Drawing Sheets

FCCP - Naïve CD4 T cells

BAM15 - Naïve CD4 T cells

Naïve CD4 T cells

Naïve CD8 T cells

NK Cells – Uncoupler Titration

METHODS AND SYSTEMS FOR DETERMINING METABOLIC POISE AND CAPACITY OF LIVING CELLS

CROSS REFERENCE TO RELATED APPLICATIONS

This application claims the benefit of U.S. Provisional Application No. 63/254,927, filed Oct. 12, 2021. The contents of the aforesaid application are hereby incorporated by reference in their entirety.

BACKGROUND

Multiple independent assays are generally needed to evaluate cells for metabolic fitness, which includes glycolytic and mitochondrial profile. Profiling from a single assay using extracellular acidification rate (ECAR) output is neither quantitative nor specific for glycolysis. In addition, response of naïve T cells (and other T cells) to certain mitochondrial uncoupling agent is not robust. Thus, there exists a need to develop new methods and systems that quantitatively determine complete bioenergetic profile, including both bioenergetic poise and bioenergetic capacity, from a single assay.

SUMMARY

In an aspect, the disclosure provides a method of evaluating the bioenergetic poise and bioenergetic capacity of a cell sample. The method comprises: acquiring a reference value for oxygen consumption ($VOC_{Ref}$); acquiring a reference value for proton efflux ($VPE_{Ref}$); contacting the cell sample with an ATP synthase inhibitor, a mitochondrial uncoupling agent, and an electron transport chain (ETC) inhibitor, sequentially, partly simultaneously, or simultaneously, each contacting forming a reaction mixture; acquiring a value for oxygen consumption for each reaction mixture ($VOC_{Mix}$); and acquiring a value for proton efflux for each reaction mixture ($VPE_{Mix}$) thereby evaluating the bioenergetic poise and bioenergetic capacity of the cell sample.

In an embodiment, the value for oxygen consumption and a value for proton efflux are acquired for a reaction mixture after the ATP synthase inhibitor is contacted with the cell sample. In an embodiment, a value for oxygen consumption and a value for proton efflux are acquired for a reaction mixture after the mitochondrial uncoupling agent is contacted with the cell sample. In an embodiment, a value for oxygen consumption and a value for proton efflux are acquired for a reaction mixture after the ETC inhibitor is contacted with the cell sample.

In an embodiment, the ATP synthase inhibitor, the mitochondrial uncoupling agent, and the ETC inhibitor are contacted with the cell sample sequentially, and (i) a value (e.g., a first value) for oxygen consumption and a value (e.g., a first value) for proton efflux are acquired for a reaction mixture (e.g., a first reaction mixture) after the ATP synthase inhibitor is contacted with the cell sample; (ii) a value (e.g., a second value) for oxygen consumption and a value (e.g., a second value) for proton efflux are acquired for a reaction mixture (e.g., a second reaction mixture) after the mitochondrial uncoupling agent is contacted with the cell sample; and (iii) a value (e.g., a third value) for oxygen consumption and a value (e.g., a third value) for proton efflux are acquired for a reaction mixture (e.g., a third reaction mixture) after the ETC inhibitor is contacted with the cell sample.

In an embodiment, oxygen consumption is not determined in a sealed system, e.g., a system allows oxygen back diffusion or substantial oxygen back diffusion to the sample. In an embodiment, oxygen consumption is oxygen depletion in the sample corrected for oxygen back diffusion to the sample. In an embodiment, oxygen consumption is oxygen depletion without being corrected for oxygen back diffusion to the sample. In an embodiment, the oxygen consumption is determined in a sealed system, e.g., a system that does not allow oxygen back diffusion or substantial oxygen back diffusion to the sample. In an embodiment, oxygen consumption equals, or substantially equals, to oxygen depletion in the sample.

In an embodiment, oxygen consumption is determined directly or indirectly, e.g., inferred from a measured oxygen gradient, e.g., within a test well, or across a capillary, or by measuring oxygen at a preselected time point.

In an embodiment, the $VOC_{Ref}$ comprises a basal or initial value for oxygen consumption for the cell sample, e.g., a value based on a measurement of oxygen consumption for the cell sample made prior to formation of a reaction mixture. In an embodiment, the oxygen consumption is measured (e.g., directly or indirectly) by oxygen consumption rate (OCR). In an embodiment, acquiring a $VOC_{Ref}$ comprises determining (e.g., measuring) a basal or initial OCR for the cell sample. In an embodiment, determining (e.g., measuring) the basal or initial OCR for the cell sample comprises sensing a metabolite (e.g., $O_2$), e.g., consumed from medium.

In an embodiment, the $VPE_{Ref}$ comprises a basal or initial value for proton efflux for the cell sample, e.g., a value based on a measurement of proton efflux for the cell sample made prior to formation of the reaction mixture. In an embodiment, the proton efflux is measured (e.g., directly or indirectly) by proton efflux rate (PER). In an embodiment, an extracellular acidification rate (ECAR) is measured to produce a value for proton efflux. In an embodiment, acquiring a $VPE_{Ref}$ comprises determining (e.g., measuring) a basal or initial PER for the cell sample. In an embodiment, determining (e.g., measuring) the basal or initial PER for the cell sample comprises sensing a metabolite or a cell constituent, e.g., disposed in medium.

In an embodiment, the $VOC_{Ref}$ and the $VPE_{Ref}$ are based on measurements of oxygen consumption and proton efflux initiated within 10 hours (e.g., within 1, 2, 3, 4, 5, 6, 7, 8, or 9 hours, within 1, 2, 5, 10, 15, 30, 45, 60, 80, or 90 minutes, within 1, 2, 5, 10, 15, 30, 45, or 60 seconds, or within 1, 10, 50, 100, 200, 400, 6011, or 800 milliseconds) of one another. In an embodiment, the $VOC_{Ref}$ and the $VPE_{Ref}$ are based on measurements of oxygen consumption and proton efflux initiated within a time period suitable for rapid instrument data acquisition, e.g., within 1, 10, 50, 100, 200, 400, 600, or 800 milliseconds. In an embodiment, the $VOC_{Ref}$ and the $VPE_{Ref}$ are based on measurements of oxygen consumption and proton efflux initiated within a time period suitable for a long-term end-point measurement, e.g., within 1, 2, 3, 4, 5, 6, 7, 8, or 9 hours.

In an embodiment, the $VOC_{Ref}$ and the $VPE_{Ref}$ are based on measurements of oxygen consumption and proton efflux initiated sequentially. In an embodiment, the $VOC_{Ref}$ and the $VPE_{Ref}$ are based on measurements of oxygen consumption and proton efflux initiated substantially simultaneously.

In an embodiment, the contacting the cell sample with the ATP synthase inhibitor, the mitochondrial uncoupling agent, and the ETC inhibitor comprises introducing (e.g., injecting, e.g., from the units (e.g., ports) in a container (e.g., cartridge) disposed above the cell sample) the ATP synthase inhibitor, the mitochondrial uncoupling agent, and the ETC inhibitor, sequentially, partly simultaneously, or simultaneously, into a well or microchamber (e.g., of a multiwell plate) disposed with the cell sample.

In an embodiment, the ATP synthase inhibitor, the mitochondrial uncoupling agent, and the ETC inhibitor are contacted with the cell sample sequentially.

In an embodiment, the ATP synthase inhibitor, the mitochondrial uncoupling agent, and the ETC inhibitor are contacted with the cell sample in the order of (from first to last):

(a) the ATP synthase inhibitor, the mitochondrial uncoupling agent, the ETC inhibitor;
(b) the ATP synthase inhibitor, the ETC inhibitor, the mitochondrial uncoupling agent;
(c) the mitochondrial uncoupling agent, the ATP synthase inhibitor, the ETC inhibitor;
(d) the mitochondrial uncoupling agent, the ETC inhibitor, the ATP synthase inhibitor;
(e) the ETC inhibitor, the ATP synthase inhibitor, the mitochondrial uncoupling agent; or
(f) the ETC inhibitor, the mitochondrial uncoupling agent, the ATP synthase inhibitor.

In an embodiment, the ATP synthase inhibitor, the mitochondrial uncoupling agent, and the ETC inhibitor are contacted with the cell sample in the order of (from first to last): the ATP synthase inhibitor, the mitochondrial uncoupling agent, the ETC inhibitor.

In an embodiment, contacting the cell sample with the ATP synthase inhibitor, the mitochondrial uncoupling agent, and the ETC inhibitor occurs within 10 hours (e.g., within 1, 2, 3, 4, 5, 6, 7, 8, or 9 hours, within 1, 2, 5, 10, 15, 30, 45, 60, 80, or 90 minutes, within 1, 2, 5, 10, 15, 30, 45, or 60 seconds, or within 1, 10, 50, 100, 200, 400, 600, or 800 milliseconds) of one another. In an embodiment, contacting the cell sample with the ATP synthase inhibitor, the mitochondrial uncoupling agent, and the ETC inhibitor occurs within a time period suitable for rapid instrument data acquisition, e.g., within 1, 10, 50, 100, 200, 400, 600, or 800 milliseconds. In an embodiment, contacting the cell sample with the ATP synthase inhibitor, the mitochondrial uncoupling agent, and the ETC inhibitor occurs within a time period suitable for a long-term end-point measurement, e.g., within 1, 2, 3, 4, 5, 6, 7, 8, or 9 hours.

In an embodiment, two or all of the ATP synthase inhibitor, the mitochondrial uncoupling agent, and the ETC inhibitor are contacted with the cell sample simultaneously or partly simultaneously.

In an embodiment, the following are contacted with the cell sample simultaneously:

(a) the ATP synthase inhibitor, the mitochondrial uncoupling agent;
(b) the ATP synthase inhibitor, the ETC inhibitor;
(c) the mitochondrial uncoupling agent, the ETC inhibitor;
(d) the ATP synthase inhibitor, the mitochondrial uncoupling agent, the ETC inhibitor.

In an embodiment, forming the reaction mixture comprises mixing any two or all of the ATP synthase inhibitor, the mitochondrial uncoupling agent, or the ETC inhibitor, prior to being contacted with the cell sample.

In an embodiment, the ATP synthase inhibitor comprises oligomycin A. In an embodiment, the ATP synthase inhibitor (e.g., oligomycin A) is present at a concentration of at least 1 nM up to the solubility limit of the ATP synthase inhibitor (e.g., oligomycin A), e.g., 1 nM to 100 mM, 10 nM to 10 mM, 0.1 μM to 1 mM, 0.1 μM to 100 μM, 0.1 μM to 10 μM, 0.2 μM to 5 μM, 0.5 μM to 2 μM, 0.2 μM to 4 μM, 0.2 μM to 3 μM, 0.2 μM to 1 μM, 0.2 μM to 0.5 μM, 4 μM to 5 μM, 3 μM to 5 μM, 2 μM to 5 μM, 1 μM to 5 μM, 0.5 μM to 5 μM, 1 μM to 3 μM, 2 μM to 4 μM, 1 μM to 2 μM, 0.5 μM to 2.5 μM, e.g., 0.2 μM, 0.5 μM, 1 μM, 1.5 μM, 2 μM, 2.5 μM, 3 μM, 3.5 μM, 4 μM. 4.5 μM, or 5 μM, in the reaction mixture. In an embodiment, wherein the ATP synthase inhibitor (e.g., oligomycin A) is present at a concentration of 1 μM to 2 μM, e.g., 1.5 μM, in the reaction mixture.

In an embodiment, the mitochondrial uncoupling agent comprises BAM15. In an embodiment, the mitochondrial uncoupling agent (e.g., BAM15) is present at a concentration of at least 1 nM up to the solubility limit of the mitochondrial uncoupling agent (e.g., BAM15), e.g., 1 nM to 100 mM, 10 nM to 10 mM, 0.1 μM to 1 mM, 0.1 μM to 100 μM, 0.1 μM to 10 μM, 0.5 μM to 10 μM, 1 μM to 8 μM, 2 μM to 6 μM, 3 μM to 4 μM, 0.5 μM to 8 μM, 0.5 μM to 6 μM, 0.5 μM to 4 μM, 0.5 μM to 2 μM, 0.5 μM to 1 μM, 8 μM to 10 μM, 6 μM to 10 μM, 4 μM to 10 μM, 2 μM to 10 μM, 1 μM to 10 μM, 1 μM to 3 μM, 2 μM to 4 μM, 3 μM to 5 μM, 4 μM to 6 μM, 5 μM to 7 μM, 6 μM to 8 μM, 7 μM to 9 μM, 2 μM to 3 μM, 1 μM to 4 μM, e.g., 0.5 μM, 1 μM, 1.5 μM, 2 μM, 2.5 μM, 3 μM, 3.5 μM, 4 μM, 5 μM, 6 μM, 7 μM, 8 μM, 9 μM, or 10 μM, in the reaction mixture. In an embodiment, the mitochondrial uncoupling agent (e.g., BAM15) is present at a concentration of 2 μM to 3 μM, e.g., 2.5 μM, in the reaction mixture.

In an embodiment, the ETC inhibitor comprises rotenone, antimycin A, or a combination thereof, optionally wherein the ETC inhibitor comprises rotenone and antimycin A. In an embodiment, the ETC inhibitor (e.g., rotenone, antimycin A, or a combination thereof) is present at a concentration of at least 1 nM up to the solubility limit of the ETC inhibitor (e.g., rotenone, antimycin A, or a combination thereof), e.g., 1 nM to 100 mM, 10 nM to 10 mM, 0.1 μM to 1 mM, 0.1 μM to 100 μM, 0.1 μM to 10 μM, 0.1 μM to 5 μM, 0.2 μM to 2 μM, 0.5 μM to 1 μM, 0.1 μM to 4 μM, 0.5 μM to 3 μM, 0.1 μM to 2 μM, 0.1 μM to 1 μM, 0.1 μM to 0.5 μM, 4 μM to 5 μM, 3 μM to 5 μM, 2 μM to 5 μM, 1 μM to 5 μM, 0.5 μM to 5 μM, 0.2 μM to 1 μM, 0.5 μM to 2 μM, 0.2 μM to 1 μM, e.g., 0.1 μM, 0.2 μM, 0.3 μM, 0.4 μM, 0.5 μM, 0.6 μM, 0.7 μM, 0.8 μM, 0.9 μM, 1 μM, 1.5 μM, 2 μM, 2.5 μM, 3 μM, 4 μM, or 5 μM, in the reaction mixture. In an embodiment, the ETC inhibitor comprises rotenone at a concentration of 0.2 μM to 1 μM (e.g., 0.5 μM) and antimycin A at a concentration of 0.2 μM to 1 μM (e.g., 0.5 μM), in the reaction mixture.

In an embodiment, forming the reaction mixture further comprises contacting the cell sample with an agent that induces an increase in energetic demand, e.g., an ionophore (e.g., monensin). In an embodiment, the ionophore (e.g., monesin) is present at a concentration of at least 1 nM up to the solubility limit of the ionophore (e.g., monesin), e.g., 1 nM to 100 mM, 10 nM to 10 mM, 0.1 μM to 1 mM, 1 μM to 100 μM, 5 μM to 100 μM, 10 μM to 80 μM, 20 μM to 60 μM, 30 μM to 50 μM, 5 μM to 80 μM, 5 μM to 60 μM, 5 μM to 40 μM, 5 μM to 20 μM, 5 μM to 10 μM, 80 μM to 100 μM, 60 μM to 100 μM, 40 μM to 100 μM, 20 μM to 100 μM, 10 μM to 100 μM, 10 μM to 40 μM, 20 μM to 60 μM, 40 μM to 80 μM, 15 μM to 25 μM, or 10 μM to 30 μM, e.g., 5 μM, 10 μM, 20 μM, 30 μM, 40 μM, 50 μM, 60 μM, 70 μM, 80 μM, 90 μM, or 100 μM, in the reaction mixture. In an embodiment, the ionophore (e.g., monesin) is present at a concentration of 10 μM to 30 μM, e.g., 20 μM, in the reaction mixture. In an embodiment, the ionophore (e.g., monesin) is prepared as a stock solution at a concentration of 200 μM to 300 μM (e.g., 240 μM) in EtOH 10% in assay media.

In an embodiment, the $VOC_{Mix}$ comprises a value for oxygen consumption for the reaction mixture, e.g., a value based on a measurement of oxygen consumption for the reaction mixture made after formation of the reaction mixture. In an embodiment, the oxygen consumption is measured (e.g., directly or indirectly) by oxygen consumption rate (OCR). In an embodiment, acquiring the $VOC_{Mix}$ comprises determining (e.g., measuring) an OCR for the reaction mixture. In an embodiment, determining (e.g., measuring) the OCR for the reaction mixture comprises sensing a metabolite (e.g., $O_2$), e.g., consumed from medium.

In an embodiment, the $VPE_{Mix}$ comprises a value for proton efflux for the reaction mixture, e.g., a value based on a measurement of proton efflux for the reaction mixture after formation of the reaction mixture. In an embodiment, the proton efflux is measured (e.g., directly or indirectly) by proton efflux rate (PER). In an embodiment, an extracellular acidification rate (ECAR) is measured to produce a value for proton efflux. In an embodiment, acquiring the PER comprises determining (e.g., measuring) a PER for the reaction mixture. In an embodiment, determining (e.g., measuring) the PER for the reaction mixture comprises sensing a cell constituent disposed in the media.

In an embodiment, the $VOC_{Mix}$ and the $VPE_{Mix}$ are based on measurements of oxygen consumption and proton efflux initiated within 10 hours (e.g., within 1, 2, 3, 4, 5, 8, or 9 hours, within 1, 2, 5, 10, 15, 30, 45, 60, 80, or 90 minutes, within 1, 2, 5, 10, 15, 30, 45, or 60 seconds, or within 1, 10, 50, 100, 200, 400, 600, or 800 milliseconds) of one another. In an embodiment, the $VOC_{Mix}$ and the $VPE_{Mix}$ are based on measurements of oxygen consumption and proton efflux initiated within a time period suitable for rapid instrument data acquisition, within 1, 10, 50, 100, 200, 400, 600, or 800 milliseconds. In an embodiment, the $VOC_{Mix}$ and the $VPE_{Mix}$ are based on measurements of oxygen consumption and proton efflux initiated within a time period suitable for a long-term end-point measurement, e.g., within 1, 2, 3, 4, 5, 6, 7, 8, or 9 hours.

In an embodiment, the $VOC_{Mix}$ and the $VPE_{Mix}$ are based on measurements of oxygen consumption and proton efflux initiated sequentially. In an embodiment, the $VOC_{Mix}$ and the $VPE_{Mix}$ are based on measurements of oxygen consumption and proton efflux initiated substantially simultaneously.

In an embodiment, the method further comprises providing the $VOC_{Ref}$, the $VPE_{Ref}$, the $VOC_{Mix}$, and the $VPE_{Mix}$ to a software program and using the software program to calculate the bioenergetic poise and bioenergetic capacity (e.g., converting to OCR and PER values) of the cell sample.

In an embodiment, the method further comprises disposing the cell sample in a well or microchamber (e.g., of a multiwell plate) prior to acquiring a $VOC_{Ref}$ and a $VPE_{Ref}$.

In an embodiment, the method further comprises acquiring a cell sample prior to disposing the cell sample in a well or microchamber (e.g., of a multiwell plate).

In an embodiment, the method further comprises acquiring a value for glycolytic proton efflux for the reaction mixture ($VglycoPE_{Mix}$). In an embodiment, the $VglycoPE_{Mix}$, is measured by glycolytic proton efflux rate (glycoPER). In an embodiment, the glycoPER is determined by mathematically removing the contribution of $CO_2$.

In an embodiment, the method further comprises acquiring a value for basal mitochondrial ATP production rate. In an embodiment, the value for basal mitochondrial ATP production rate is acquired by subtracting the minimum oxygen consumption rate (oligo OCR) from the oxygen consumption rate (OCR) before formation of the reaction mixture (basal OCR) and multiplying by a constant. In an embodiment, the oligo OCR is the minimum OCR after the ATP inhibitor (e.g., oligomycin) is contacted with the cell sample. In an embodiment, the constant is 2.75 (called P/O Ratio)*2 (to convert oxygen atoms to oxygen molecules).

In an embodiment, the basal OCR is a measurement (e.g., any previous measurement, e.g., the last measurement or an average of a number of measurements), of OCR, before the first contacting (e.g., injection) of any of the ATP synthase, the uncoupling agent, or the ETC inhibitor.

In an embodiment, the method further comprises acquiring a value for basal glycolytic ATP production rate. In an embodiment, the value for basal glycolytic ATP production rate is acquired using the measurements of extracellular acidification rate (ECAR) before formation of the reaction mixture (e.g., before contacting the cell sample with the ATP synthase inhibitor (e.g., oligomycin A)) and converting the proton efflux rate (PER).

In an embodiment, converting the PER comprises considering the buffer capacity of the medium employed in the method and the volume of the well or microchamber that holds the cell sample and discounting the contribution of extracellular $CO_2$ production, e.g., calculated from the measurements of the basal oxygen consumption rate (OCR) and the minimum measurement after contacting the cell sample with the ETC inhibitor (e.g., rotenone, antimycin, or a combination thereof) and before any following contacting step (e.g., injection), e.g., contacting the cell sample with an ionophore (e.g., monensin). In an embodiment, the minimum measurement is an average of the lower range after the ETC inhibitor is contacted with the cell sample.

In an embodiment, the method further comprises acquiring a value for maximal respiratory capacity. In an embodiment, the value for maximal respiratory capacity is acquired by using the maximal measurement of oxygen consumption rate (OCR) after contacting the cell with the uncoupling agent (e.g., BAM15) and discounting the minimum measurement of oxygen consumption rate (OCR) after contacting the cell sample with the ETC inhibitor (e.g., rotenone, antimycin, or a combination thereof) and before any following contacting step (e.g., injection), e.g., contacting the cell sample with an ionophore (e.g., monensin).

In an embodiment, the method further comprises acquiring a value for reserve aerobic capacity (also known as spare respiratory capacity). In an embodiment, the value for reserve aerobic capacity is acquired by determining the difference between maximal measurement of oxygen consumption rate (OCR) after contacting the cell sample with the uncoupling agent (e.g., BAM15) and last measurement of oxygen consumption rate (OCR) before contacting the cell sample with the first of any of the ATP synthase inhibitor (e.g., oligomycin A), the uncoupling agent (e.g., BAM15), or the ETC inhibitor (e.g., rotenone, antimycin, or a combination thereof). In an embodiment, the value for reserve aerobic capacity is expressed in units of ATP production rate multiplying by the factor 5.5.

In an embodiment, the method further comprises acquiring a value for maximal mitochondrial bioenergetic capacity. In an embodiment, the value for maximal mitochondrial bioenergetic capacity is acquired by using the maximal measurement of oxygen consumption rate (OCR) after contacting the cell sample with the uncoupling agent (e.g., BAM15) and discounting the minimum measurement after contacting the cell sample with the ATP synthase (e.g., oligomycin A) and before any following contacting (e.g., injection) step (e.g., the contacting (e.g., injection) of the ETC inhibitor) and multiplying by 5.5.

In an embodiment, the method further comprises acquiring a value for compensatory (or maximal glycolytic capacity). In an embodiment, the value for compensatory (or maximal glycolytic capacity) is acquired using the maximal measurement of proton efflux rate (PER) after contacting the cell sample with the ETC inhibitor (e.g., rotenone, antimycin A, or a combination thereof), optionally further after contacting the cell sample with an ionophore (e.g., monensin).

In an embodiment, the method further comprises acquiring a reference value for extracellular acidification ($VEA_{Ref}$); and acquiring a value for extracellular acidification for the reaction mixture ($VEA_{Mix}$).

In an embodiment, the cell sample comprises a plurality of cells disposed in media. In an embodiment, the cell sample comprises immune cells. In an embodiment, the immune cells are immune effector cells.

In an embodiment, the cell sample comprises T cells (e.g., CD4+ T cells, CD8+ T cells. In an embodiment, the cells comprise T helper cells ($T_H$ cells or CD4+ T cells, e.g., Th1, Th2, Th17, Th9, or Tfh), cytotoxic T cells ($T_C$ cells or CD8+ T cells), memory T cells (e.g., central memo T cells ($T_{CM}$ cells, CD45RO+CCR7+CD62L+), effector memory T cells ($T_{EM}$ cells, $T_{EMRA}$ cells, CD45RO+CCR7− CD62L−), tissue resident memory T cells ($T_{RM}$, CD103+), or virtual memory T cells (e.g., CD4 virtual memory T cells or CD8 virtual memory T cells)), regulatory T cells (Treg, e.g., CD4+ FOXP3+Tregs or CD4+FOXP3−Tregs), innate-like T cells, natural killer T cells (NKT cells), mucosal associated invariant T cells, gamma delta T cells, or any combination thereof. In an embodiment, the cell sample comprises engineered T cells, e.g., CAR-T cells or TCR-T cells. In an embodiment, the cell sample comprises primary T cells, e.g., primary naïve T cells (e.g., human or murine primary naïve T cells).

In an embodiment, the cell sample comprises NK cells or CD56+CD3− cells. In an embodiment, the NK cells comprise $CD56^{bright}$ NK cells, $CD56^{dim}$ NK cells, or a combination thereof. In an embodiment, the cell sample comprises engineered NK cells, e.g., CAR-NK cells or TCR-NK cells. In an embodiment, the cell sample comprises CAR-NK cells. In an embodiment, the cell sample comprises primary NK cells, e.g., primary naïve NK cells (e.g., human or murine primary naïve NK cells).

In an embodiment, the cell sample comprises immortalized immune cells, e.g., THP1 cells.

In an embodiment, the cell sample comprises suspension cells. In an embodiment, the cell sample comprises cells having an average size of 15 μm or less, e.g., 14 μm or less, 13 μm or less, 12 μm or less, 11 μm or less, 10 μm or less, 9 μm or less, 8 μm or less, 7 μm or less, 6 μm or less, 5 μm or less, or 4 μm or less, in diameter, e.g., 4 μm to 12 μm, 4 μm to 10 μm, 4 μm to 8 μm, 5 μm to 7 μm, 5 μm to 6 μm, or 6 μm to 7 μm, e.g., in diameter.

In an embodiment, the cell sample comprises cells that are suitable for a cell therapy, e.g., an adoptive cell therapy (ACT). In an embodiment, the cell sample comprises cells from a subject, e.g., a subject having, or is at risk of having, a disorder, e.g., a cancer or an immune disorder.

In an embodiment, the cell sample comprises at least 10, 20, 30, 40, 50, 60, 70, 80, or 90% (by number) immune cells (e.g., T cells or NK cells).

In an embodiment, the method is performed in a single assay.

In an aspect, the disclosure provides a method of monitoring the production of an engineered cell product comprising evaluating the bioenergetic poise and bioenergetic capacity of a cell sample of the engineered cell product in accordance with a method described herein, thereby monitoring the production of the engineered cell product.

In an aspect, the disclosure provides a method optimizing a cell design, comprising evaluating the bioenergetic poise and bioenergetic capacity of a cell sample having the cell design in accordance with a method described herein, thereby optimizing the cell design.

In an aspect, the disclosure provides a method optimizing a culture medium, comprising evaluating the bioenergetic poise and bioenergetic capacity of a cell sample that has been cultured in the culture medium in accordance with a method described herein, thereby optimizing the culture medium.

In an aspect, the disclosure provides a method optimizing a culture condition, comprising evaluating the bioenergetic poise and bioenergetic capacity of a cell sample that has been cultured under the culture condition in accordance with a method described herein, thereby optimizing the culture condition.

In an aspect, the disclosure provides a method of evaluating the quality of a cell preparation, comprising evaluating the bioenergetic poise and bioenergetic capacity of a cell sample of the cell preparation in accordance with a method described herein, thereby evaluating the quality of the cell preparation.

In an aspect, the disclosure provides a method of making engineered cells (e.g., CAR T cells or CAR NK cells), comprising modifying cells (e.g., T cells or NK cells) to express a transgene encoding a protein of interest (e.g., a CAR); and evaluating the bioenergetic poise and bioenergetic capacity of a cell sample of the engineered cells in accordance with a method described herein, thereby making the engineered cells (e.g., CAR T cells or CAR NK cells).

In an aspect, the disclosure provides a method of treating a disorder in a subject, comprising evaluating the bioenergetic poise and bioenergetic capacity of a cell sample of a cell therapy product in accordance with a method described herein; administering the cell therapy product to the subject, thereby treating the disorder in the subject.

In an embodiment, the disorder is a cancer. In an embodiment, the disorder is a solid tumor. In an embodiment, the disorder is a hematological cancer.

In an embodiment, the disorder is an autoimmune disease. In an embodiment, the disorder (or a treatment therefor) comprises tissue replacement. In an aspect, the disclosure provides a cell therapy product for use in a method of treating a disorder in a subject, wherein the method comprises evaluating the bioenergetic poise and bioenergetic capacity of a cell sample of the cell therapy product in accordance with a method described herein.

In an aspect, the disclosure provides a method of evaluating a metabolic response of a cell to a physiologically relevant condition, comprising evaluating the bioenergetic poise and bioenergetic capacity of a cell sample in accordance with a method described herein, thereby evaluating the metabolic response.

In an embodiment, the physiologically relevant condition is associated with a tumor microenvironment, e.g., reduced $O_2$, reduced/altered metabolic substrates, decreased pH, or a combination thereof.

In an aspect, the disclosure provides a system (e.g., an apparatus) for evaluating the bioenergetic poise and bioenergetic capacity of a cell sample, comprising: (i) a stage adapted to support a multiwell plate; (ii) a sensor adapted to sense a metabolite, or a cell constituent, associated with the cell sample, consumed from the medium or disposed in the medium, e.g., in a well or microchamber of the multiwell plate; and (iii) a dispensing system adapted to introduce fluids into the well or microchamber, wherein the stage, sensor, and dispensing system cooperate to: acquire a reference value for oxygen consumption ($VOC_{Ref}$) and a reference value for proton efflux ($VPE_{Ref}$) for the cell sample using the sensor; use the dispending system to contact the cell sample with an ATP synthase inhibitor, a mitochondrial uncoupling agent, and an electron transport chain (ETC) inhibitor, thereby forming a reaction mixture; acquire a value for oxygen consumption for the reaction mixture ($VOC_{Mix}$) and a value for proton efflux for the reaction mixture ($VPE_{Mix}$) using the sensor, thereby evaluating the bioenergetic poise and bioenergetic capacity of the cell sample.

In an embodiment, the dispensing system comprises at least one unit (e.g., a port) disposed above the well or microchamber. In an embodiment, the sensor comprises an optical sensor. In an embodiment, the sensor is adapted to sense a fluorophore. In an embodiment, the system further comprising a computer module and software adapted to calculate the bioenergetic poise and bioenergetic capacity based on information communicated to the computer module by the sensor.

BRIEF DESCRIPTION OF THE DRAWINGS

FIG. 5A) or the ECAR (mpH/min; FIG. 5B) values are indicated on the y-axis.

DETAILED DESCRIPTION

Figure 1A:
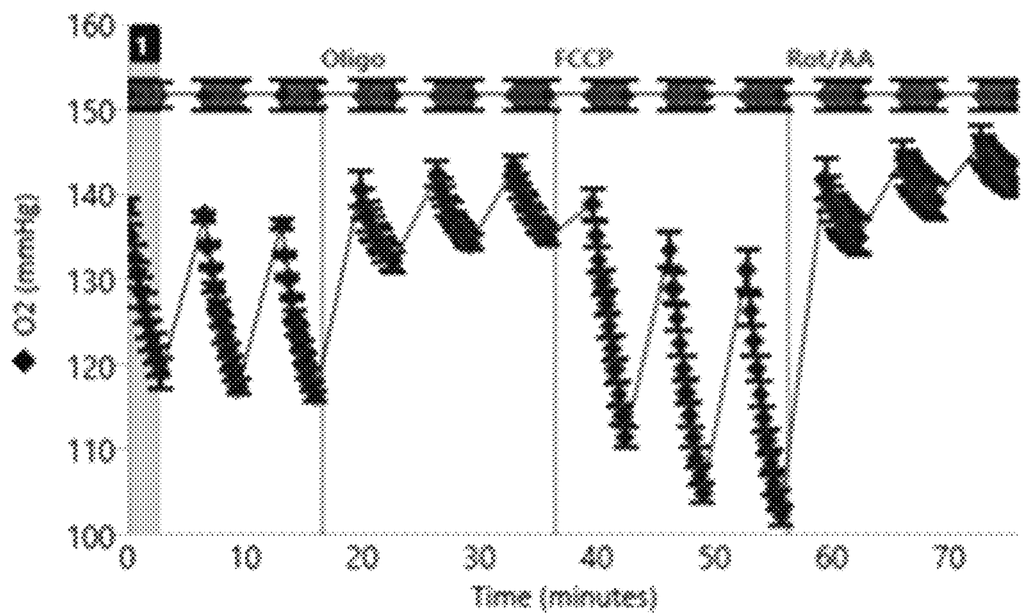
FIGS. 1A-1C are graphs for a metabolic profiling assay using 2 μM FCCP to measure uncoupled respiration in epithelioid carcinoma Panc-1 cells (ATCC, CRL-1469). Extracellular oxygen levels (FIG. 1A), Oxygen Consumption Rate (OCR) (FIG. 1B), and OCR (point to point) (FIG. 1C) are shown.

Metabolic Fitness of T cells is a broad concept used to describe, for example, the optimal metabolic phenotype of immunotherapy cell products for increased anti-tumor potency. Metabolic Fitness parameters can include, for example, basal bioenergetic phenotype (basal mitochondrial ATP Production Rate+glycolytic ATP Production Rate), Mitochondrial Maximal Respiratory Capacity, and Spare Respiratory Capacity. Standard Seahorse XF analyzers combined with existing kits allow measurements of these parameters from independent assays, requiring double the amount of material at least to calculate all the assay outputs. In addition, performance of certain mitochondrial uncoupler in human and mice T cells is poor, resulting in underestimation of Maximal Respiratory Capacity even after extensive titration and overestimation of non-mitochondrial respiration required to calculate glycolytic ATP Production Rate. The methods and systems described herein allow obtaining robust measurements of Metabolic Fitness parameters from a single assay with the minimum amount of biological material and without onerous reagent re-optimization. In an embodiment, a method described herein is performed in a single assay.

Traditional methods of evaluating metabolic/bioenergetic poise for cell samples typically rely on measurements of oxygen consumption rate (OCR) and extracellular acidification rate (ECAR), which is a less specific measure of glycolytic activity. Without wishing to be bound by theory, it is believed that in an embodiment the methods described herein (i) provide a more complete bioenergetic picture, (ii) use more accurate glycolytic parameters, and/or (iii) use an uncoupler more suited to the measurement of immune cells, compared to traditional methods. In an embodiment, the method provides a more complete bioenergetic picture and uses more accurate glycolytic parameters, for example, for immune cells. The methods described herein are based, at least in part, on the discovery that mitochondrial uncoupling agent, BAM15, demonstrated more robust performance than FCCP, in immune cells, which contributes to the profound improvement of the methods described herein over traditional methods.

In an embodiment, the methods described herein provide a more complete bioenergetic picture compared to traditional methods. In an embodiment, the method combines the measurements of bioenergetic work (e.g., the amount of ATP being generated by the cell), bioenergetic poise (e.g., the proportion of ATP generate by glycolysis of oxidative phosphorylation), and bioenergetic capacity (e.g., the level of increase in glycolytic and mitochondrial activity that the cell can affect in response to increased energy demand).

In another embodiment, the methods described herein use more accurate glycolytic parameters compared to traditional methods. In an embodiment, the method uses glycolytic proton efflux rate (glycoPER, which is equivalent to glycolytic ATP production rate) instead of extracellular acidification rate (ECAR). ECAR typically does not account for (i) the buffering capacity of the measurement media or (ii) the contribution of aerobically generated $CO_2$ to measured acidification. In an embodiment of the methods described herein, buffer factor is mathematically addressed (presented as PER) and the $CO_2$ contribution is removed to provide a glycoPER value. For example, the buffer factor is typically dependent of the assay media that is used and is predetermined in the assay and used to convert ECAR to PER (e.g., PER=ECAR*Buffer Factor*Volume of "microchamber' during measurement). In an embodiment, the method uses ATP production rate as a parameter to describe metabolic activity and poise as opposed to the ECAR/OCR plot. Without wishing to be bound by theory, it is believed that in an embodiment, the methods described herein can generate both metabolic poise and maximal respiration and/or reserve capacity (aerobic and/or glycolytic) from the same well. In an embodiment, BAM15 is used as a mitochondrial uncoupling agent. In an embodiment, maximal glycolytic capacity is also demonstrated using monensin (or a similar ionophore).

In yet another embodiment, the methods described herein uses a mitochondrial uncoupling agent suitable for more accurate estimate for maximal and/or reserve capacity for the cells described herein (e.g., immune cells, e.g., T cells and NK cells). For example, mitochondrial uncoupling agent, BAM15, is less toxic to immune cells (e.g., T cells and NK cells), e.g., compared to FCCP. Without wishing to be bound by theory, it is believed that in an embodiment the structure of BAM15 allows to maintain maximal rate of mitochondrial oxygen consumption during the period (e.g., 3 minutes) of the instrument measurement, and when added at the optimized concentration, avoiding an underestimation of maximal and/or reserve mitochondrial bioenergetic capacity in immune cells.

Definitions

Unless defined otherwise, all technical and scientific terms used herein have the same meaning as commonly understood by one of ordinary skill in the art to which the invention pertains.

As used herein, the articles "a" and "an" refer to one or to more than one (e.g., to at least one) of the grammatical object of the article.

"About" and "approximately" as the term used herein shall generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the term used herein refers to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third-party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent. In an embodiment, directly acquiring encompasses a direct measurement. In an embodiment, indirectly acquiring encompasses an inference.

"Acquiring a sample" as the term used herein refers to obtaining possession of a sample, e.g., a sample described herein, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third-party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material; dissecting or scraping a tissue; separating or purifying a substance; combining two or more separate entities into a mixture; or performing a chemical reaction that includes breaking or forming a covalent or non-covalent bond.

"Basal mitochondrial ATP production rate" as the term used herein refers to the rate of ATP production by mitochondria in a cell sample before the cell sample is contacted with an ATP synthase inhibitor, a mitochondrial uncoupling agent, and an electron transport chain (ETC) inhibitor to form a reaction mixture. In an embodiment, the basal mitochondrial ATP production rate is calculated by subtracting the minimum oxygen consumption rate (oligo OCR) to a measurement (e.g., the last measurement, or an average of a number of measurements) of oxygen consumption rate before the first contacting of the cell sample with any of the ATP synthase inhibitor, mitochondrial uncoupling agent, or ETC inhibitor (basal OCR) and multiplying by a constant between 2.45 and 2.86 (called P/O ratio)*2 (to convert oxygen atoms to oxygen molecules). In an embodiment, the constant is 2.75.

"Bioenergetic capacity" as the term used herein refers to the level of increase in glycolytic and/or mitochondrial activity that a cell can affect, utilize, and/or induce. In an embodiment, the bioenergetic capacity is determined in response to increased energy demand and/or in response to inhibition/perturbation of energy-generation. In an embodiment, the bioenergetic capacity comprises a value for oxygen consumption (e.g., an oxygen consumption rate (OCR)) and a value for proton efflux (e.g., a proton efflux rate (PER)). In an embodiment, the value for oxygen consumption (e.g., OCR) is in response to mitochondrial uncoupling. In an embodiment, the value for proton efflux (e.g., PER) in in response to ATPase inhibition. In an embodiment the PER is glycolytic PER (glycoPER), which mathematically removes the contribution of $CO_2$.

"Basal glycolytic ATP production rate" as the term used herein refers to the rate of ATP production by glycolysis (e.g., when glucose is converted into lactate) in a cell sample before the cell sample is contacted with an ATP synthase inhibitor, a mitochondrial uncoupling agent, and an electron transport chain (ETC) inhibitor to form a reaction mixture. In an embodiment, the basal glycolytic ATP production rate is calculated using the measurements of extracellular acidification rate (ECAR) before contacting the cell sample with an ATP synthase inhibitor, and converting the rate of proton efflux considering buffer capacity of media employed in the assay and the microchamber volume of the multiwell plate and discounting the contribution of extracellular $CO_2$ production that is calculated from the measurements of the basal oxygen consumption prior to, and subsequent to, contacting the cell sample with an ETC inhibitor, delivering a values that informs $CO_2$ contribution to measured acidification which in turn is transposed into an ATP production rate.

"Bioenergetic poise" as the term used herein refers to the balance between aerobic and glycolytic energy production. In an embodiment, the bioenergetic poise describes the proportion of ATP generated by glycolysis of oxidative phosphorylation. In an embodiment, the bioenergetic poise comprises a relationship, e.g., a ratio, between ATP made by mitochondria and ATP made by glycolysis, between ATP made by mitochondria and total ATP production, between ATP made by glycolysis and total ATP production, or any combination thereof.

"Bioenergetic work" as the term used herein refers to the amount of ATP being generated by a cell.

"Cancer" and "tumor" at the terms used interchangeably herein refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers.

"CAR NK cell therapy" as the term used herein refers to a therapy that uses a CAR NK cell.

"CAR T cell therapy" as the term used herein refers to a therapy that uses a CAR T cell.

"Cell sample" as the term used herein refers to a sample that comprises a cell. In an embodiment, the cell sample comprises a plurality of cells. In an embodiment, the cell is disposed in a medium.

"Chimeric antigen receptor" or "CAR" as the term used herein refers to a recombinant polypeptide comprising an extracellular antigen binding domain, a transmembrane domain and an intracellular signaling domain. Chimeric antigen receptors can redirect immune cells toward cells expressing target antigens.

"Chimeric antigen receptor NK cell" or "CAR NK cell" as the term used herein refers to an NK cell that has been genetically engineered to express a chimeric antigen receptor (CAR).

"Chimeric antigen receptor T cell" or "CAR T cell" as the term used herein and refers to a T cell that has been genetically engineered to express a chimeric antigen receptor (CAR).

"Compensatory glycolytic capacity" and "maximal glycolytic capacity" as the terms used interchangeably herein refer to the capacity of a cell sample to compensate energy production through glycolysis after inhibition of mitochondrial ATP production and/or increasing energetic demand. Compensatory glycolytic capacity can be expressed as a percentage of basal glycolysis. In an embodiment, the compensatory glycolytic capacity is calculated using the maximal measurement of proton efflux rate (PER) after the cell sample is contacted with an ETC inhibitor or an ionophore.

"Maximal respiratory capacity" as the term used herein refers to the theoretical capacity of a cell sample to produce ATP by oxidative phosphorylation. In an embodiment, the maximal respiratory capacity is calculated using the maximal measurement of oxygen consumption rate (OCR) after the cell sample is contacted with a mitochondrial uncoupling agent and discounting the minimum measurement of oxygen consumption rate (OCR) after the cell sample is contacted with an ETC inhibitor, and before any further injections.

"Or" is used herein to mean, and is used interchangeably with, the term "and/or", unless context clearly indicates otherwise. The use of the term "and/or" in some places herein does not mean that uses of the term "or" are not interchangeable with the term "and/or" unless the context clearly indicates otherwise.

"Primary cell" as the term used herein refers to a cell isolated or harvested directly from a subject, organ, or tissue. For example, primary cells can be isolated from blood obtained from a living subject. Primary cells can be isolated or harvested using enzymatic or mechanical methods. Once isolated or harvested, primary cells can be cultured in media containing essential nutrients and growth factors to support proliferation. Primary cells can be suspension cells that do not require attachment for growth (e.g., anchorage-independent cells) or adherent cells that require attachment for growth (e.g., anchorage-dependent cells).

"Reserve aerobic capacity" and "spare respiratory capacity" as the terms used herein refer to the capacity of a cell sample to produce the extra amount of ATP by oxidative phosphorylation, for example, in case of an acutely increased energy demand. In an embodiment, the reserve aerobic capacity or spare respiratory capacity is calculated from the difference between the maximal measurement of oxygen consumption rate (OCR) after the cell sample is contacted with a mitochondrial uncoupling agent and discounting the basal measurement of oxygen consumption rate before injection of any reagent and can be expressed in multiple units including, for example, units of oxygen consumption or ATP production.

"Reserve glycolytic capacity" as term used herein refers to the capacity of a cell sample to produce the extra amount of ATP by glycolysis, for example, in case of an acutely increased energy demand. In an embodiment, the reserve glycolytic capacity is calculated as the difference between the maximal glycolytic capacity and basal glycolytic ATP production.

"Sample" as the term used herein refers to a biological sample obtained or derived from a source of interest. In an embodiment, the source of interest comprises an organism, such as an animal or human. The source of the sample can be blood or a blood constituent; a bodily fluid; a solid tissue as from a fresh, frozen and/or preserved organ, tissue, biopsy, resection, smear, or aspirate; or cells from any time in gestation or development of a subject. In an embodiment, the source of the sample is blood or a blood constituent. In an embodiment, the sample is a primary sample, e.g., obtained directly from a source of interest by any appropriate means. In an embodiment, the sample is a preparation that is obtained by processing (e.g., by removing one or more components of and/or by adding one or more agents to) a primary sample.

"T cell receptor NK cell" or "TCR NK cell" as the term used herein and refers to an NK cell that has been genetically engineered to express a T cell receptor (TCR).

"T cell receptor T cell" or "TCR T cell" as the term used herein and refers to a T cell that has been genetically engineered to express a T cell receptor (TCR).

"TCR NK cell therapy" as the term used herein refers to a therapy that uses a TCR NK cell.

"TCR T cell therapy" as the term used herein refers to a therapy that uses a TCR T cell.

Cell Samples

The methods and systems described herein can be used to evaluate the bioenergetic poise and bioenergetic capacity of various cell samples.

In an embodiment, the cell sample is obtained or derived from a subject. In an embodiment, the subject is a human. In an embodiment, the subject is a non-human animal. In an embodiment, the subject is a mouse. In an embodiment, the subject has, or is at risk of having, a disorder, e.g., a disorder described herein.

In an embodiment, the cell sample comprises a primary cell. In an embodiment, the cell sample comprises a cell isolated or harvested directly from a living tissue or organ. In an embodiment, the cell sample comprises a cultured cell. In an embodiment, the cell sample comprises a primary cell, or a cell isolated or harvested directly from a living tissue or organ, and then cultured ex vivo. In an embodiment, the cell sample comprises an immortalized cell. In an embodiment, the cell sample comprises a cell that has been modified, e.g., genetically engineered for heterologous expression of a gene of interest. In an embodiment, the cell sample comprises a suspension cell. In an embodiment, the cell sample comprises an adherent cell. In an embodiment, the cell sample comprises a stem cell. In an embodiment, the cell sample comprises a cell derived from a stem cell. In an embodiment, the cell sample comprises a medium, e.g., a culture medium or a growth medium. In an embodiment, the cell is disposed in the medium. In an embodiment, the cell sample comprises a plurality of cells, e.g., a plurality of cells described herein.

In an embodiment, the cell sample comprises an immune cell. In an embodiment, the immune cell is immune effector cells. In an embodiment, the immune cell is a primary immune cell. In an embodiment, the immune cell is an immortalized immune cell, e.g., a THP1 cell. In an embodiment, the cell sample comprises a plurality of immune cells. In an embodiment, the immune cell is a genetically engineered immune cell. In an embodiment, 50% or more (e.g., 60%, 70%, 80%, 85%, 90%, 95%, 98%, 99%, or 100%) of the cells in the cell sample are immune cells.

In an embodiment, the immune cell is a T cell. Exemplary T cells include, but are not limited to helper cell ($T_H$ cell or CD4+ T cell, e.g., Th1, Th2, Th17, Th9, or Tfh), cytotoxic T cell ($T_C$ cell or CD8+ T cell), memory T cell central memory T cell ($T_{CM}$ cell, CD45RO±CCR7+CD62L+), effector memory T cell ($T_{EM}$ cell, $T_{EMRA}$ cell, CD45RO+ CCR7−CD621L−), tissue resident memory T cell ($T_{RM}$, CD103+), or virtual memory T cell (e.g., CD4 virtual memory T cell or CD8 virtual memory T cell)), regulatory T cell (Treg, e.g., CD4+FOXP3+Treg or CD4-1-FOXP3− Treg), innate-like T cell, natural killer T cell (NKT cell), mucosal associated invariant T cell, and gamma delta T cell. In an embodiment, the T cell is a CD4+ T cell. In an embodiment, the T cell is a CD8+ T cell.

In an embodiment, the T cell is a primary T cell. In an embodiment, the T cell is a naïve T cell. In an embodiment, the T cell is a primary naïve T cell (e.g., a human or murine primary naïve T cell). In an embodiment, the T cell is genetically engineered T cell. In an embodiment, the T cell is a CAR-1' cell. In an embodiment, the T cell is a TCR-T cell. In an embodiment, the cell sample comprises a plurality of T cells. In an embodiment, 50% or more (e.g., 60%, 70%, 80%, 85%, 90%, 95%, 98%, 99%, or 100%) of the cells in the cell sample are T cells.

In an embodiment, the immune cell is a natural killer cell (NK cell). In an embodiment, immune cell is a CD56+CD3− cell. In an embodiment, the NK cell is a $CD56^{bright}$ NK cell. In an embodiment, the NK cell is a $CD56^{dim}$NK cell.

In an embodiment, the NK cell is a primary NK cell. In an embodiment, the NK cell is a naïve NK cell. In an embodiment, the NK cell is a primary naïve NK cell (e.g., a human or murine primary naïve NK cell). In an embodiment, the NK cell is a genetically engineered NK cell. In an embodiment, the NK cell is a CAR-NK cell. In an embodiment, the NK cell is a TCR-NK cell. In an embodiment, the cell sample comprises a plurality of NK cells. In an embodiment, 50% or more (e.g., 60%, 70%, 80%, 85%, 90%, 95%, 98%, 99%, or 100%) of the cells in the cell sample are NK cells.

In an embodiment, the cell has a size of 15 μm or less, e.g., 14 μm or less, 13 μm or less, or less, 11 μm or less, 10 μm or less, 9 μm or less, 8 μm or less, 7 μm or less, 6 μm or less, 5 μm or less, or 4 μm or less, in diameter, e.g., 3 μm to 15 μm, 4 μm to 12 μm, 4 μm to 10 μm, 5 μm to 10 μm, 4 μm to 8 μm, 5 μm to 7 μm, 5 μm to 6 μm, or 6 μm to 7 μm, in diameter. In an embodiment, the cell has the same, or substantially the same, size as a typical T cell or NK cell.

In an embodiment, the cell sample comprises a plurality of cells, and the cells have an average size of 15 μm or less, 14 μm or less, 13 μm or less, 12 μm or less, 11 μm or less, 10 μm or less, 9 μm or less, 8 μm or less, 7 μm or less, 6 μm or less, 5 μm or less, or 4 μm or less, in diameter, e.g., 3 μm to 15 μm, 4 μm to 12 μm, 4 μm to 10 μm, 5 μm to 10 μm, 4 μm to 8 μm, 5 μm to 7 μm, 5 μm to 6 μm, or 6 μm to 7 μm, in diameter. In an embodiment, the cell sample comprises a plurality of cells, and on average the cells have the same, or substantially the same, size as a typical T cell or NK cell.

In an embodiment, the cell is suitable for use in a therapy for treating a disorder in a subject. In an embodiment, the cell is suitable for a cell therapy, e.g., an adoptive cell therapy (ACT). In an embodiment, the cell is suitable for an immunotherapy, e.g., a cancer immunotherapy. In an embodiment, the immunotherapy is an autologous immunotherapy. In an embodiment, the immunotherapy is an allogeneic immunotherapy. In an embodiment, the disorder is a cancer. In an embodiment, the cancer is a solid tumor. In an embodiment, the cancer is a hematological cancer, e.g., a leukemia, a lymphoma, or a myeloma. In an embodiment, the cell is isolated or harvested from the subject. In an embodiment, the cell is further modified, e.g., genetically engineered to express a gene of interest.

A reaction mixture described herein can be formed by contacting a cell sample that has not been contacted with any of an ATP synthase inhibitor, a mitochondrial uncoupling agent, or an ETC inhibitor with an ATP synthase inhibitor, a mitochondrial uncoupling agent, or an ETC inhibitor. A reaction mixture described herein can also be formed by contacting a previously formed reaction mixture (e.g., a cell sample that has been contacted with an ATP synthase inhibitor, a mitochondrial uncoupling agent, or an ETC inhibitor) with an ATP synthase inhibitor, a mitochondrial uncoupling agent, or an ETC inhibitor. For example, a reaction mixture described herein can be formed by contacting a cell sample that has not been contacted with an ATP synthase inhibitor, a mitochondrial uncoupling agent, or an ETC inhibitor with an ATP synthase inhibitor. As another example, a reaction mixture described herein can be formed by contacting a cell sample that has been contacted with an ATP synthase inhibitor with a mitochondrial uncoupling agent. As yet another example, a reaction mixture described herein can be formed by contacting a cell sample that has been contacted with an ATP synthase inhibitor and a mitochondrial uncoupling agent with an ETC inhibitor.

In an embodiment, the methods and systems described herein can use a plurality of reaction mixtures derived from a single cell sample that has been contacted with an ATP synthase inhibitor, a mitochondrial uncoupling agent, or an ETC inhibitor, sequentially. In an embodiment, each sequential contacting step forms a reaction mixture that can be used in accordance with a method or system described herein.

ATP Synthase Inhibitors

ATP synthase inhibitors can be used in the methods and systems described herein.

In an embodiment, the ATP synthase inhibitor is suitable for use in measuring a cell described herein, e.g., an immune cell (e.g., a T cell or an NK cell). The ATP synthase inhibitor can be introduced by pre-addition or by in-assay injection.

In an embodiment, the ATP synthase inhibitor is an oligomycin or a derivative thereof. Exemplary oligomycins include, but are not limited to, oligomycin A, oligomycin B, oligomycin C, oligomycin D, oligomycin E, oligomycin F, rutamycin B, 44-homooligomycin A, and 44-homooligmycin B, or any combination thereof. Other ATP synthase inhibitors that can be used in the methods and systems described herein are described, e.g., in Hong and Pedersen, Microbiol Mol Biol Rev. 2008 December; 72 (4):590-641, which is incorporated by reference in its entirety.

In an embodiment, the oligomycin is oligomycin A or a derivative thereof. Oligomycin can inhibit state 3 (phosphorylating) respiration. Oligomycin A inhibits ATP synthase by blocking its proton channel ($F_O$ subunit), which is necessary for oxidative phosphorylation of ADP to ATP. The inhibition of ATP synthesis by oligomycin A can significantly reduce electron flow through the electron transport chain; however, electron flow is not stopped completely due to a process known as proton leak or mitochondrial uncoupling.

In an embodiment, the ATP synthase inhibitor (e.g., oligomycin A) is used at a final concentration of at least 1 nM up to the solubility limit of the ATP synthase inhibitor (e.g., oligornycin A). In an embodiment, the ATP synthase inhibitor (e.g., is used at a final concentration of 1 nM to 100 mM, e.g., 10 nM to 10 mM, 0.1 μM to 1 mM, 0.1 μM to 100 μM, 0.1 μM to 10 μM, 0.2 μM to 5 μM, 0.5 μM to 2 μM, 0.2 μM to 4 μM, 0.2 μM, to 3 μM, 0.2 μM to 1 μM, 0.2 μM to 0.5 μM, 4 μM to 5 μM, 3 μM to 5 μM, 2 μM to 5 μM, 1 μM to 5 μM, 0.5 μM to 5 μM, 1 μM to 3 μM, 2 μM to 4 μM, 1 μM to 2 μM, 0.5 μM to 2.5 μM, e.g., 0.2 μM, 0.5 μM, 1 μM, 1.5 μM, 2 μM, 2.5 μM, 3 μM, 3.5 μM, 4 μM, 4.5 μM, or 5 μM, in the reaction mixture. In an embodiment, the ATP synthase inhibitor (e.g., oligomycin A) is used at a final concentration of 1 μM to 2 μM, e.g., 1.5 μM.

Mitochondrial Uncoupling Agents

Mitochondrial uncoupling agents can be used in the methods and systems described herein.

Oxidative phosphorylation involves the coupling of nutrient oxidation and concomitant oxygen consumption to ATP production through a proton cycle across the mitochondrial inner membrane. Any pathway that enables proton re-entry into the matrix independent of ATP synthase uncouples mitochondrial oxygen consumption from ATP production. Pharmacological uncouplers (also known as mitochondrial uncoupling agents) are small molecules that allow for proton to re-enter to the mitochondrial matrix driven by its concentration gradient end electrochemical potential. Pharmacological uncouplers are generally protonophores, small molecule organic compounds, typically lipophilic weak acids that utilize the pH gradient in the mitochondria to shuttle protons from the inner membrane space to the mitochondrial matrix. To have a good performance the uncouplers typically need to increase mitochondrial oxygen consumption and depolarize mitochondrial membrane without affecting plasma membrane conductance and have a broad effective range. In an embodiment, the mitochondrial uncoupling agent is an agent that is capable of permeabilizing the inner mitochondrial membrane (IMM).

In an embodiment, the mitochondrial uncoupling agent is suitable for use in measuring a cell described herein, e.g., an immune cell (e.g., a T cell or an NK cell). The mitochondrial uncoupling agent can be introduced by pre-addition or by in-assay injection.

In an embodiment, the mitochondrial uncoupling agent is a BAM family of compounds, e.g., BAM15 or a derivative thereof. BAM15, (2-fluorophenyl)-{6-[(2-fluorophenyl) amino](1,2,5-oxadiazolo[3,4-e]pyrazin-5-yl)}amine is an exemplary uncoupler that is able to sustain the maximal rate of mitochondrial oxygen consumption without affecting plasma membrane potential. Studies suggested that the furazan, pyrazine, and aniline rings as well as pKa are responsible for maintaining its effective protonophore activity. BAM15 is described, e.g., in Kenwood et al. Bioorganic & Medicinal Chemistry Letters, Volume 25, Issue 21, 2015, Pages 4858-4861; Kenwood et al. Volume 3, Issue 2, 2014, Pages 114-123; U.S. Application Publication No. 2017/0240563, the contents of which are incorporated by reference in their entirety.

In an embodiment, the methods and systems described herein replace the commonly used uncoupler FCCP for the compound BAM15. In an embodiment, BAM15 induces a more robust measurement of maximal respiratory capacity when used in T cells than FCCP, minimize the need for uncoupler titration in each sample test, reducing the amount of biological material required for the assay, and provides an uncouple response that is more stable during the 3 min of analyzer time measurement allowing obtention of accurate measurement of T cell metabolic fitness. In an embodiment, the use of BAM15 instead of FCCP allows calculating glycolytic ATP production rate and compensatory glycolytic activity even when the uncoupler is injected before rotenone and antimycin A injection, providing a complete metabolic profile of T cells with data obtained from a single well.

In an embodiment, the mitochondrial uncoupling agent (e.g., BAM15) is used at a final concentration of at least 1 nM up to the solubility limit of the mitochondrial uncoupling agent (e.g., BAM15). In an embodiment, the mitochondrial uncoupling agent (e.g., BAM15) is used at a final concentration of 1 nM to 100 mM, e.g., 10 nM to 10 mM, 0.1 μM to 1 mM, 0.1 μM to 100 μM, 0.1 μM to 10 μM, 0.5 μM to 10 μM, 1 μM to 8 μM, 2 μM to 6 μM, 3 μM to 4 μM, 0.5 μM to 8 μM, 0.5 μM to 6 μM, 0.5 μM to 4 μM, 0.5 μM to 2 μM, 0.5 μM to 1 μM, 8 μM to 10 μM, 6 μM to 10 μM, 4 μM to 10 μM, 2 μM to 10 μM, 1 μM to 10 μM, 1 μM to 3 μM, 2 μM to 4 μm, 3 μM to 5 μM, 4 μM to 6 μM, 5 μM to 7 μM, 6 μM 8 μM, 7 μM to 9 μM, 2 μM to 3 μM, 1 μM to 4 μM, e.g., 0.5 μM, 1 μM, 1.5 μM, 2 μM, 2.5 μM, 3 μM, 3.5 μM, 4 μM, 5 μM, 6 μM, 7 μM, 8 μM, 9 μM, or 10 μM, in the reaction mixture. In an embodiment, the mitochondrial uncoupling agent BAM15) is used at a final concentration of 2 μM to 3 μM, e.g., 2.5 μM.

In an embodiment, the mitochondrial uncoupling agent (e.g., BAM15) is used at a final concentration that maintains the maximal rate of mitochondrial oxygen consumption during the period of instrument measurement (e.g., about 3 minutes) and avoids an underestimation of maximal and/or reserve mitochondrial bioenergetic capacity in immune cells.

Electron Transport Chain (ETC) Inhibitors

Electron transport chain (ETC) inhibitors can be used in the methods and systems described herein.

The electron transport chain is a series of protein complexes that transfer electrons from electron donors to electron acceptors via redox reactions (both reduction and oxidation occurring simultaneously) and couples this electron transfer with the transfer of protons (Ft ions) across a membrane. The energy from the redox reactions create an electrochemical proton gradient that drives the synthesis of ATP. The complexes in the electron transport chain harvest the energy of the redox reactions that occur when transferring electrons from a low redox potential to a higher redox potential, creating an electrochemical gradient, which drives the synthesis of ATP via coupling with oxidative phosphorylation with ATP synthase.

In an embodiment, the ETC inhibitor is suitable for use in measuring a cell described herein, e.g., an immune cell (e.g., a T cell or an NK cell). The ETC inhibitor can be introduced by pre-addition or by in-assay injection.

In an embodiment, the ETC inhibitor comprises a mitochondrial complex I (e.g., rotenone). In an embodiment, the ETC inhibitor comprises a mitochondrial complex III inhibitor (e.g., antimycin A). In an embodiment, the ETC inhibitor comprises a mitochondrial complex I (e.g., rotenone) and a mitochondrial complex HI inhibitor (e.g., antimycin A).

In an embodiment, the ETC inhibitor comprises rotenone, antimycin A, or a combination thereof. In an embodiment, the ETC inhibitor comprises both rotenone and antimycin A.

In an embodiment, the ETC inhibitor rotenone, antimycin A, or a combination thereof) is used in a final concentration in the reaction mixture that results in the inhibition of electron transport chain in the cell sample. In an embodiment, the ETC inhibitor (e.g., rotenone, antimycin A, or a combination thereof) is used at a final concentration of at least 1 nM up to the solubility limit of the ETC inhibitor (e.g., rotenone, antimycin A, or a combination thereof), in an embodiment, the ETC inhibitor (e.g., rotenone, antimycin A, or a combination thereof) is used at a final concentration of 1 nM to 100 mM, e.g., 10 nM to 10 mM, 0.1 μM to 1 mM, 0.1 μM to 100 μM, 0.1 μM to 10 μM, 0.1 μM to 5 μM, e.g., 0.2 μM to 2 μM, 0.5 μM to 1 μM, 0.1 μM to 4 μM, 0.1 μM to 3 μM, 0.1 μM to 2 μM, 0.1 μM to 1 μM, 0.1 μM to 0.5 μM, 4 μM to 5 μM, 3 μM to 5 μM, 2 μM to 5 μM, 1 μM to 5 μM, 0.5 μM to 5 μM, 0.2 μM to 1 μM, 0.5 μM to 2 μM, 0.2 μM to 1 μM, 1 μM to 20 μM, 1 μM to 10 μM, or 5 μM to 15 μM, e.g., 0.1 μM, 0.2 μM, 0.3 μM, 0.4 μM, 0.5 μM, 0.6 μM, 0.7 μM, 0.8 μM, 0.9 μM, 1 μM, 1.5 μM, 2 μM, 2.5 μM, 3 μM, 4 μM, or 5 μM, 6 μM, 7 μM, 8 μM, 9 μM, 10 μM, 11 μM, 12 μM, 13 μM, 14 μM, 15 μM, 16 μM, 17 μM, 18 μM, 19 μM or 20 μM, in the reaction mixture. In an embodiment, the ETC inhibitor comprises rotenone and antimycin A. In an embodiment, the ratio of rotenone to antimycin A is 1:1, 1:2, 1:3, 1:4, 1:5, 2:1, 3:1, 4:1, or 5:1. In an embodiment, the ratio of rotenone to antimycin A is 1:1.

In an embodiment, the ETC inhibitor (rotenone, antimycin A, or a combination thereof) is used at a final concentration of 0.1 μM to 1 μM, e.g., 0.5 μM. In an embodiment, rotenone is used at a final concentration of 0.1 μM to 1 μM, e.g., 0.5 μM. In an embodiment, antimycin A is used at a final concentration of 0.1 μM to 1 μM, e.g., 0.5 μM. In an embodiment, a combination of rotenone and antimycin A is used at a final concentration of 0.2 μM to 2 μM, e.g., 1 μM (e.g., 0.5 μM).

Materials

1. An analytical tool suitable for performing analysis in accordance with embodiments of the disclosure may be, e.g., any one of the following instruments:

a. Agilent Seahorse XFp Analyzer b. Agilent Seahorse XF HS Mini Analyzer c. Agilent Seahorse XFe96 Analyzer d. Agilent Seahorse XFPro Analyzer.

Each of these instruments allow for one to determine oxygen consumption rate and extracellular acidification rate of a cell sample in a well of a specialized multiwell plate. The instrument includes (i) a stage adapted to support a multiwell plate; (ii) a sensor adapted to sense changes in oxygen level and pH (proton concentration) of the cellular media associated with the metabolic activity of the cell sample in a well of the multiwell plate; and (iii) a dispensing system adapted to introduce fluids into the well. Components of the apparatus are described in, e.g., U.S. Pat. Nos. 7,276,351 and 8,658,349. As discussed below, the stage, sensor, and dispensing system cooperate to simultaneously measure an initial oxygen consumption rate and an initial extracellular acidification rate of the cell sample using the sensor. Thereafter, the dispensing system is used to sequentially administer to the cell sample a mitochondrial ATP synthase inhibitor (Oligomycin A), the mitochondrial uncoupling agent BAM15 and the mixture of mitochondrial Complex I and Complex III inhibitors (rotenone and antimycin A, respectively) followed by the simultaneous measurement of oxygen consumption rate and extracellular acidification rate after each dispensing using the sensors. An additional modulator reagent can be optionally dispensed before the dispensing of described reagents or the extracellular membrane ionophore monensin can be injected after the injection of rotenone/antimycin A to the cells and in each of the cases, the same measurements of oxygen consumption rate and extracellular acidification rate after each dispensing are performed.

2. Cell culture media. Typically for immune cells, Immunocult XF T cell expansion media (Stem Cell Technologies) is used but other cell culture media like RPMI available from Gibco supplemented with 10% FBS, 10 mM glucose, 2 mM glutamine and 1 mM pyruvate can be employed depending on cell type recommendations.

3. Assay media, typically RPMI supplemented with 1 mM HEPES buffer but omitting sodium bicarbonate that is replaced by an osmotic equivalent concentration of NaCl and pH to 7.4 is used (available as Agilent Seahorse XF RPMI pH 7.4) supplemented with 10 mM Glucose, 2 mM glutamine, and 1 mM pyruvate.

4. Assay cartridge appropriate for the instrument being used, e.g., XFe96 FluxPak.

5. Cells in culture (typically immune mammalian T cells or natural killer cells (NK cells)) although not limited to this. The number of cells required varies based on the instrument used, the type of multiwell plate and the type of cell. Typically, the number is between 30,000 and 200,000 per well.

6. Reagents

Oligomycin A, BAM15, and rotenone+antimycin A mixture available as water-soluble formulation as part of the Agilent Seahorse XF T cell Metabolic Profiling Kit or the Agilent Seahorse XFp T cell Metabolic Profiling Kit. Monensin powder (available from Sigma).

Exemplary Protocol

1) Frozen stocks of immune cells like T cells are thaw in pre-warmed Immunocult XF T Cell Expansion medium, resuspended in the same media at a cell density of 1 million/mL, transfer to a T75 culture flask and incubate overnight in $CO_2$ incubator. Alternatively, T cells or other immune cells can be freshly isolated from tissues as human blood or mice spleens. Isolated cells are resuspended in XF T Cell Expansion medium at densities between 1-3 million cells/mL for at least 1 hr.

2) After incubation period in culture medium, cells are centrifuged, resuspended in assay media as a density that allows the seeding of the desired cell number in 30-50 μL of volume, and seeded in multiwell plates pre-coated with PDL or Cell Tak. Multiwell plates are centrifuged, assay media is added to complete recommended volume for the particular plate type (typically 200 μL) and incubated at 37 C in a non-CO2 incubator for 45 min.

3) The appropriate instrument is programmed with command instructions to conduct, e.g., three measurements, inject sequentially the solution from the ports in a cartridge disposed above the cell sample in a well and conduct 3 measurements after each injection.

4) Oligomycin A stock solution is prepared to a working concentration of 13.5 μM in assay media. BAM15 stock solutions are prepared at an optimized concentration (generally 25 μM for human and mice T cells) and rotenone plus antimycin A mix stock solution is prepared to a working concentration of 5.5 μM each. Monensin stock solution is prepared as a stock 240 μM in EtOH 10% in assay media.

5) A sufficient volume of the working solution is added to an assay cartridge such that upon injection the working solution is diluted into the assay medium to the final desired concentration. For example, in human T cells, the final desired concentration is 1.5 μM of oligomycin A, 2.5 μM of BAM15 and 0.5 μM of Rotenone plus Antimycin A mixture and 20 μM of Monensin. These concentrations were determined by titration for optimal effectiveness.

6) The hydrated assay cartridge containing the indicated reagent is loaded into the instrument.

7) The metabolic profile of the cell sample may be determined by calculating:

i) Basal mitochondrial ATP production rate, calculated subtracting the minimum oxygen consumption rate after injection of oligomycin A and before any other injection (oligo OCR) to a measurement (e.g., the last measurement, or an average of a number of measurements) of oxygen consumption rate before the first injection of reagents (basal OCR) and multiplying by a constant between 2.45 and 2.86, e.g., the constant 2.75 (called average P/O Ratio, i.e., yield of ATP/O consumed)*2 (to convert oxygen atoms to oxygen molecules);

ii) Basal glycolytic ATP Production Rate is calculated using the measurements of extracellular acidification rate before the Oligomycin Injection and converting the rate of Proton Efflux (considering Buffer Capacity of media employed in the assay and the microchamber volume of the multiwell plate) and discounting the contribution of extracellular $CO_2$ production that is calculated from the measurements of the basal rate of Oxygen Consumption rate and the minimum measurement after the injection of rotenone/antimycin A and before any following injection;

iii) Maximal Respiratory Capacity is calculated using the maximal measurement of oxygen consumption rate after BAM15 injection and discounting the minimum measurement of Oxygen consumption rate after the injection of rotenone/antimycin A and before any following injection;

iv) Reserve Aerobic Capacity (also known as Spare Respiratory Capacity) is calculated as the difference between maximal measurement of oxygen consumption rate after BAM15 injection and a measurement (e.g., the last measurement, or an average of a number of measurements) of oxygen consumption rate before the first injection. Aerobic Reserve Capacity can be expressed in units of Rates of ATP production multiplying by the P/O ratio*2;

v) Maximal Mitochondrial Bioenergetic capacity is calculated using the maximal measurement of oxygen consumption rate after BAM15 injection and discounting the minimum measurement after the injection of Oligomycin A and before any following injection and Multiplying by P/O Ratio*2;

vi) Compensatory (or Maximal Glycolytic Capacity) is calculated using the maximal measurement of PER after rotenone +antimycin injection (or after monensin injection).

vii) Reserve Glycolytic Capacity. Calculated as the difference between Maximal Glycolytic Capacity and basal glycoPER.

EXAMPLES

Example 1: Performance of Mitochondrial Uncouplers in Immune Cells

Figure 1B:
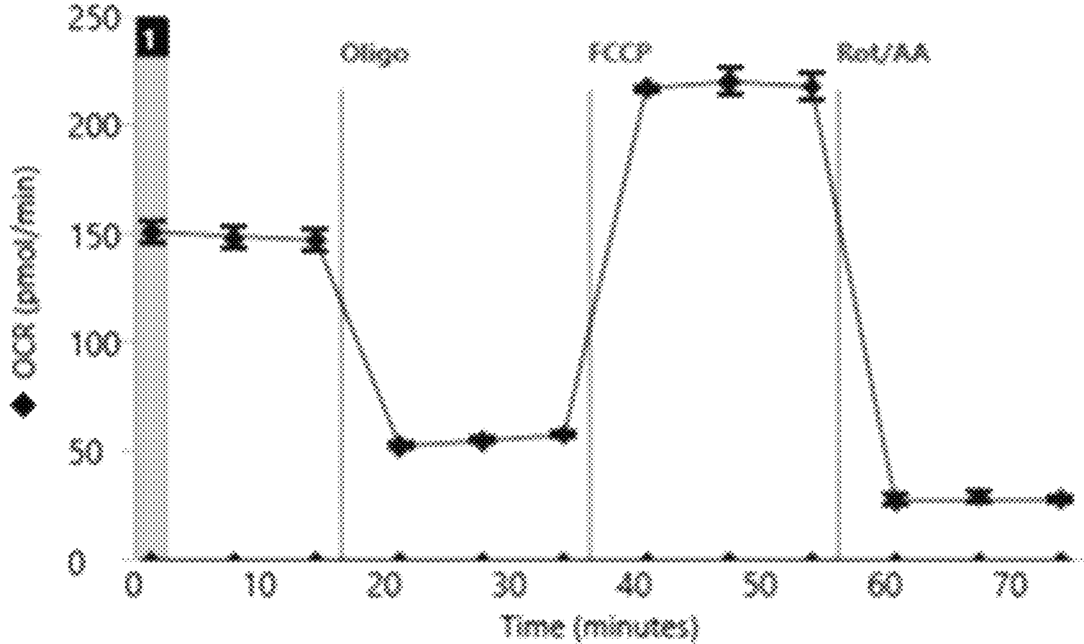
Figure 1C:
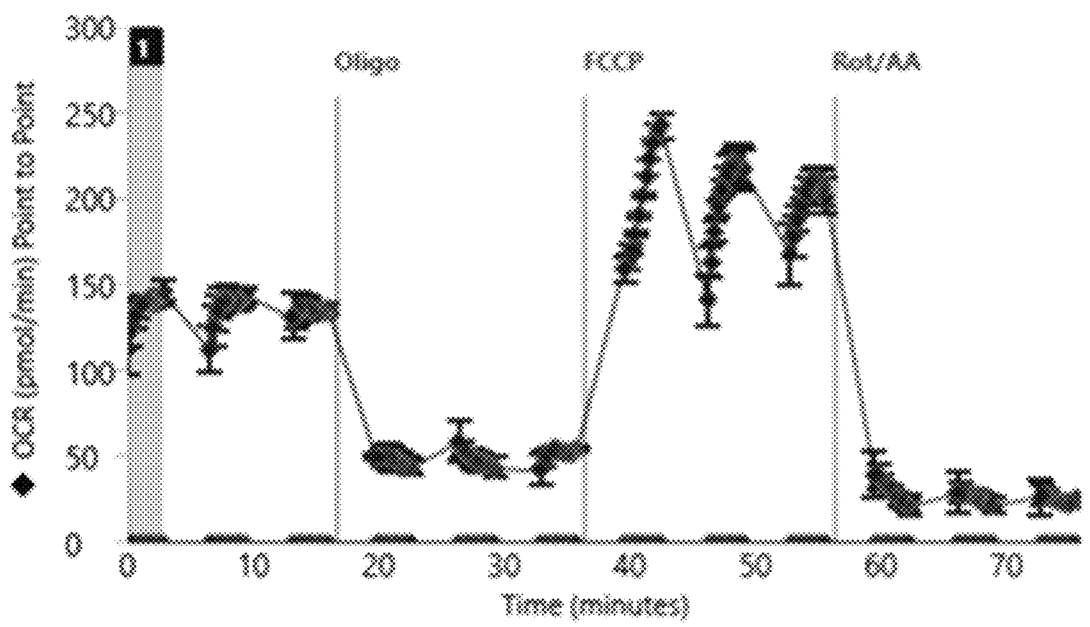
Figure 1D:
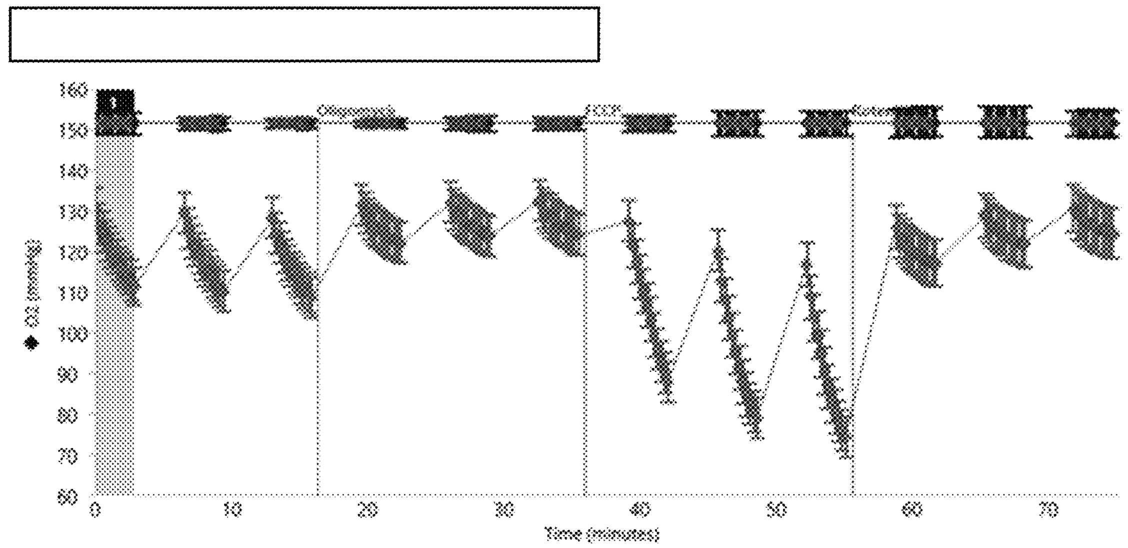
FIGS. 1D-1F are graphs for a metabolic profiling assay using 0.75 μM FCCP to measure uncoupled respiration in mouse myoblast C2C12 cells (ATCC, CRL-1772). Extracellular oxygen levels (FIG. 1D), Oxygen Consumption Rate (OCR) (FIG. 1E), and OCR (point to point) (FIG. 1F) are shown.
Figure 1E:
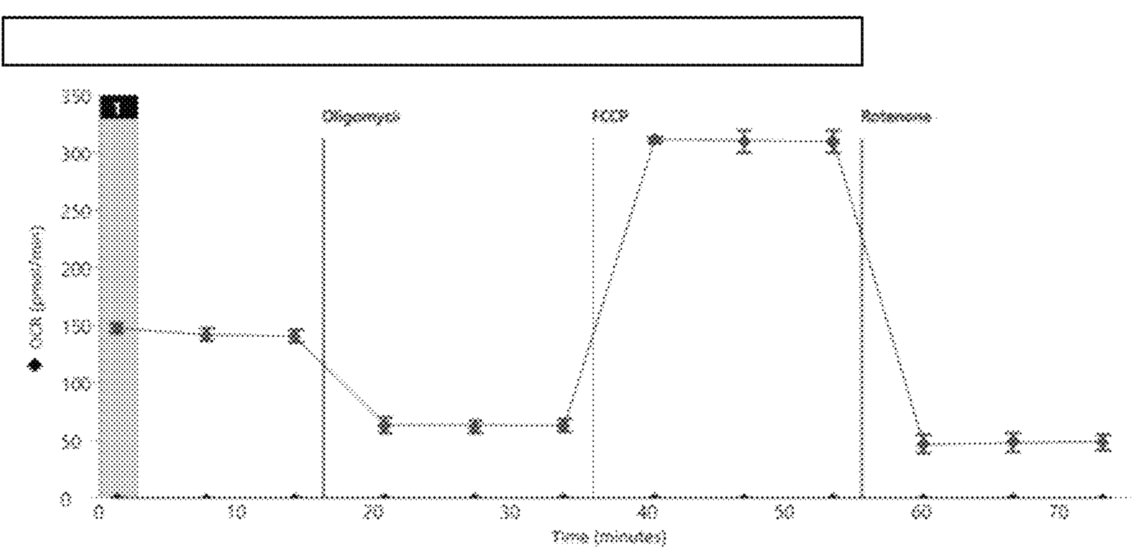
Figure 1F:
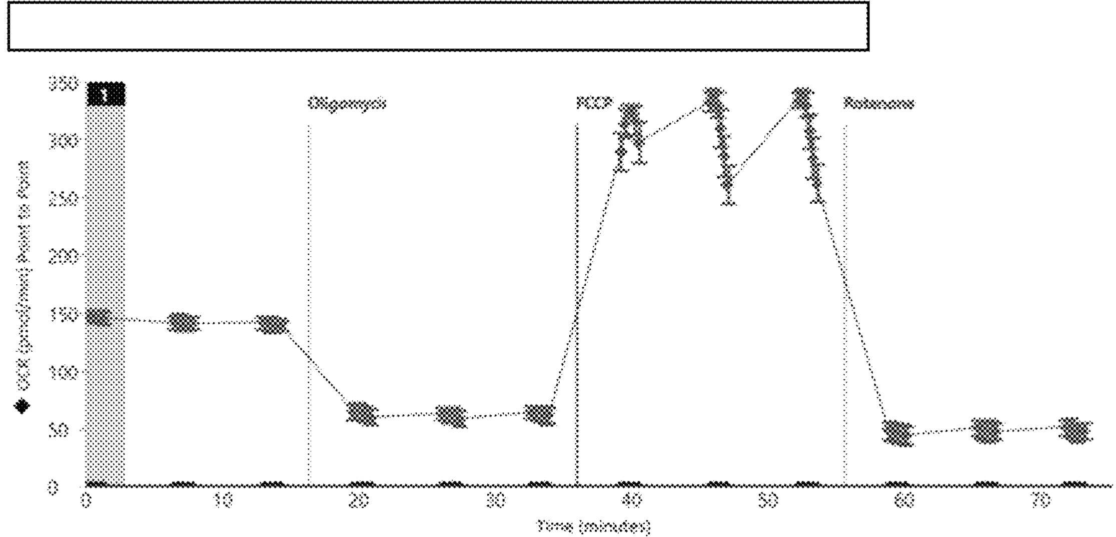
Figure 2A:
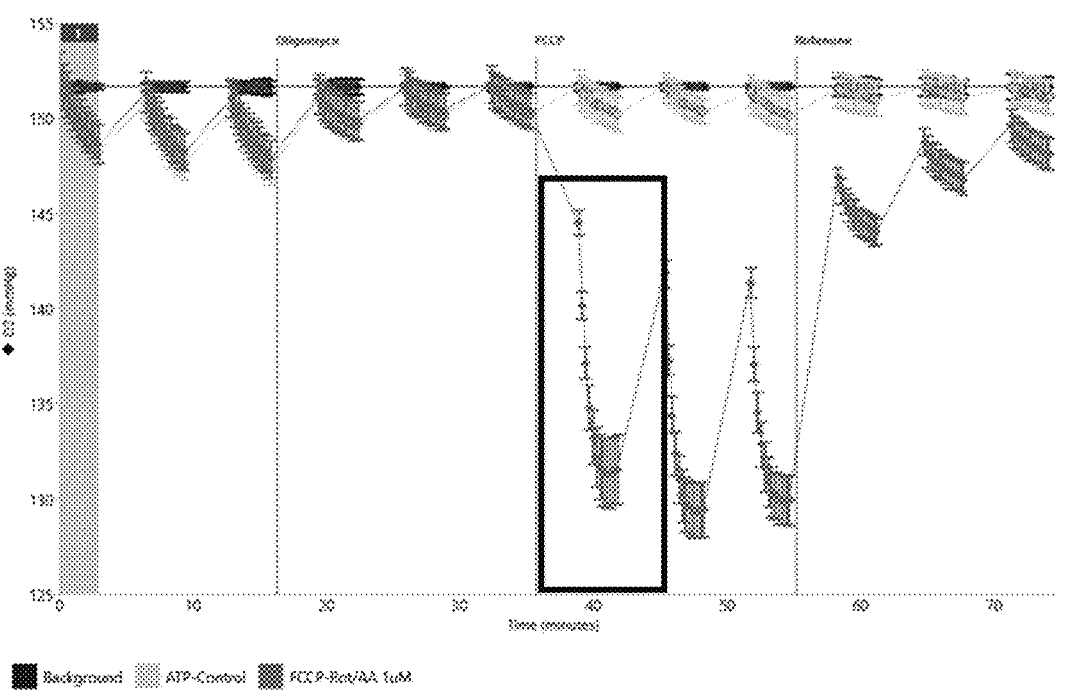
FIG. 2A-2C are graphs for a metabolic profiling assay using FCCP to measure uncoupled respiration in Human Peripheral Blood CD4+ T cells (Stem Cell Technologies, Cat. No. 70026). Extracellular oxygen levels (FIG. 2A), OCR (FIG. 2B), and OCR (point to point) (FIG. 2C) are shown.
Figure 2B:
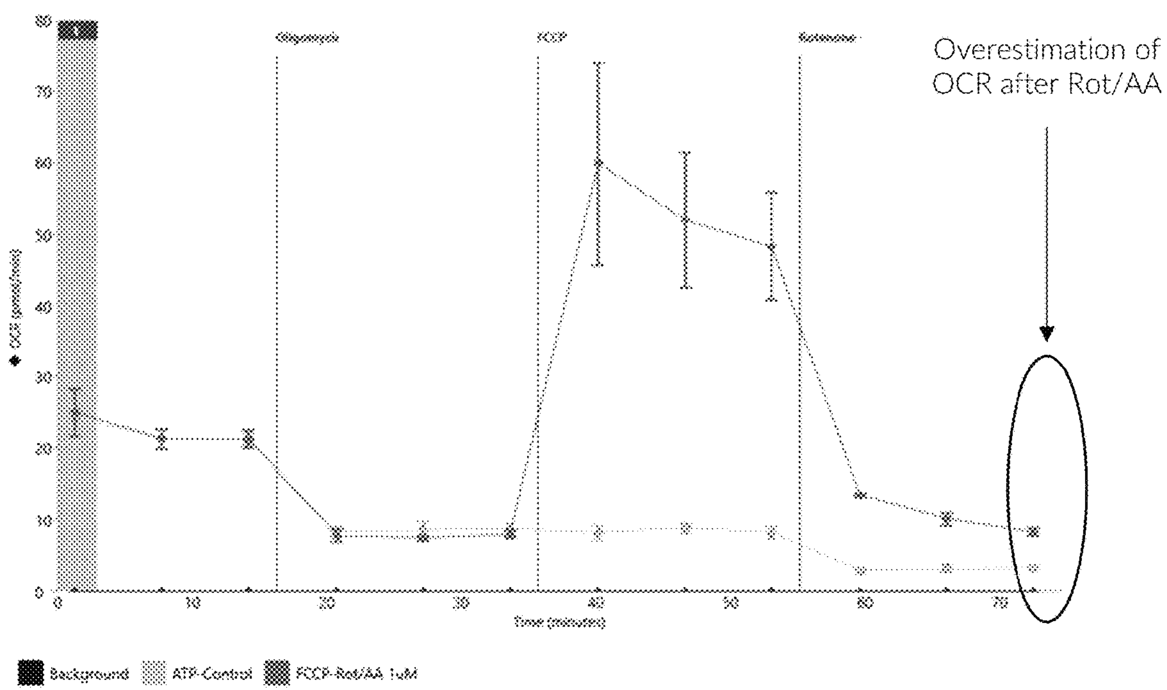
Figure 2C:
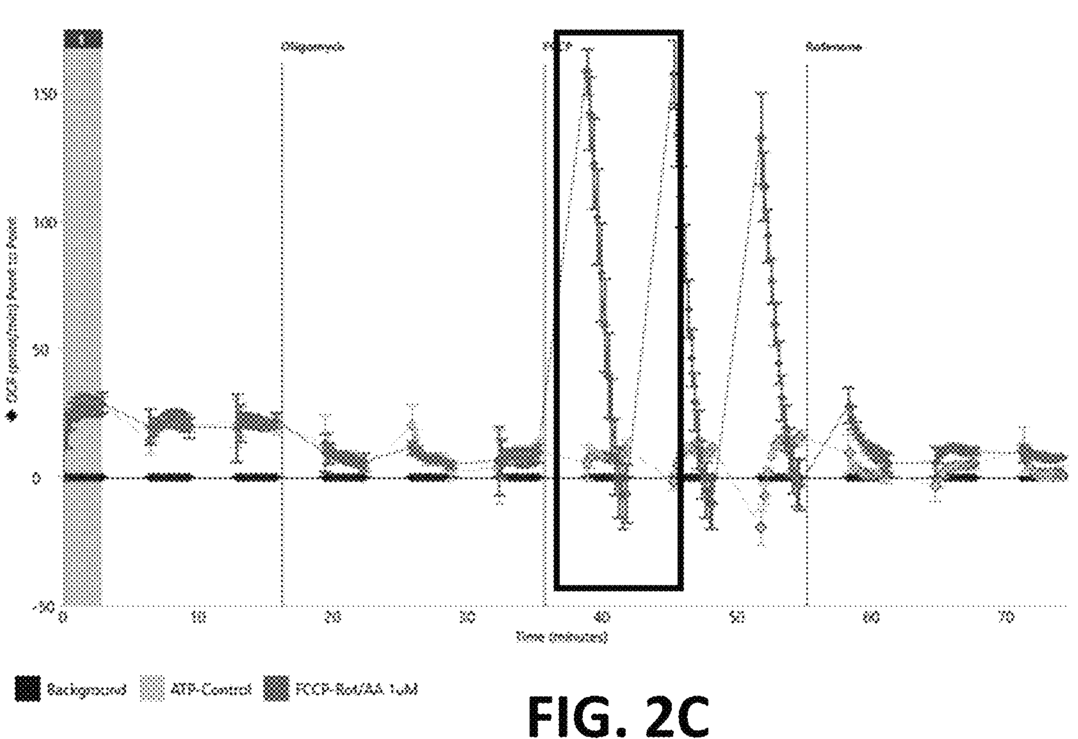

Uncoupled respiration measurements were measured in adherent cells epithelioid carcinoma Panc-1 cells (ATCC, CRL-1469) with FCCP. Cells were cultured in Dulbecco's Modified Eagle's Medium (DMEM) supplemented with 10% FBS at 37 C, 5% $CO_2$ incubator according to supplier information. Day before the assay, cells were detached using Trypsin-EDTA solution and seeded in XFe96 cell culture miniplates (Agilent) at 10,000 cells/well. Cells were incubated for 18 hr at 37 C, 5% $CO_2$ incubator. To measure OCR, cells were washed, and cell culture medium was replaced by XF DMEM pH 7.4 supplemented with 10 mM glucose, 2 mM glutamine and 1 mM pyruvate. When FCCP was added to the assay sample, the Panc-1 cells exhibited a robust increase in oxygen consumption (FIGS. 1A-1C). Similar responses are observed in multiple primary and immortalized cells tested. For example, the results for mouse myoblast C2C12 cells (ATCC, CRL-1772) are shown in FIGS. 1D-1F. When FCCP was added to an assay sample comprising immune cells (e.g., T cells), the cells exhibited inconsistent uncoupled respiration during the 3 min of the measurement (FIGS. 2A, 2C), with an overestimation of OCR after the rotenone+antimycin A injection (FIG. 2B).

Figure 3A:
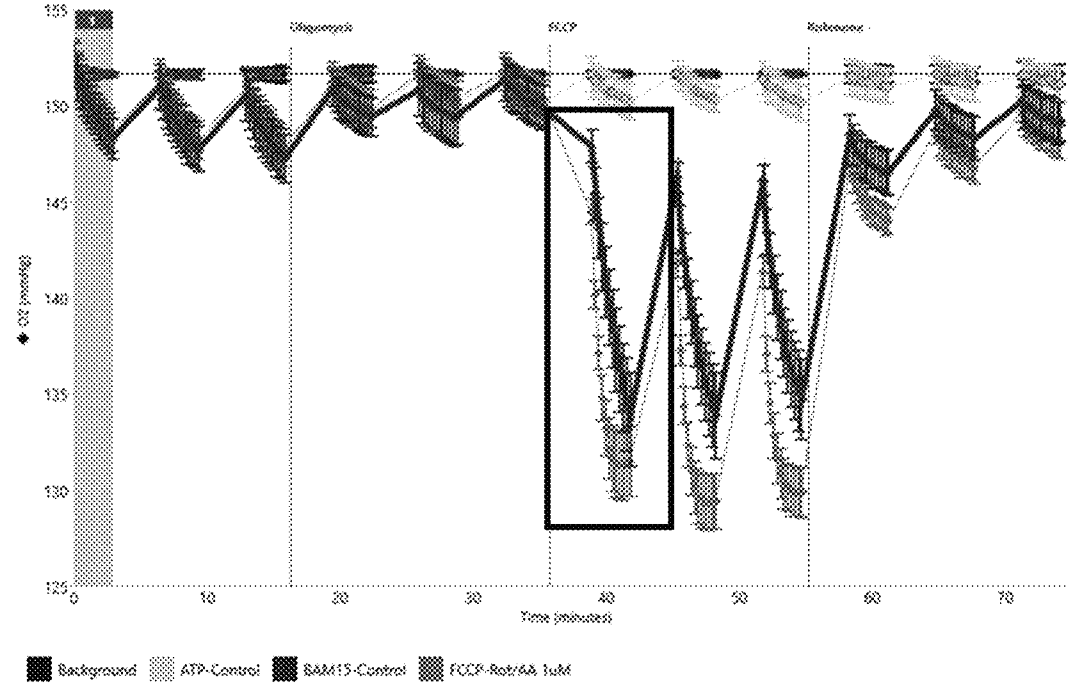
FIG. 3A-3C are graphs for a metabolic profiling assay using BAM15 to measure uncoupled respiration in Human Peripheral Blood CD4+ T cells (Stem Cell Technologies, Cat. No. 70026) Extracellular oxygen levels (FIG. 3A), OCR (FIG. 3B), and OCR (point to point) (FIG. 3C) are shown.
Figure 3B:
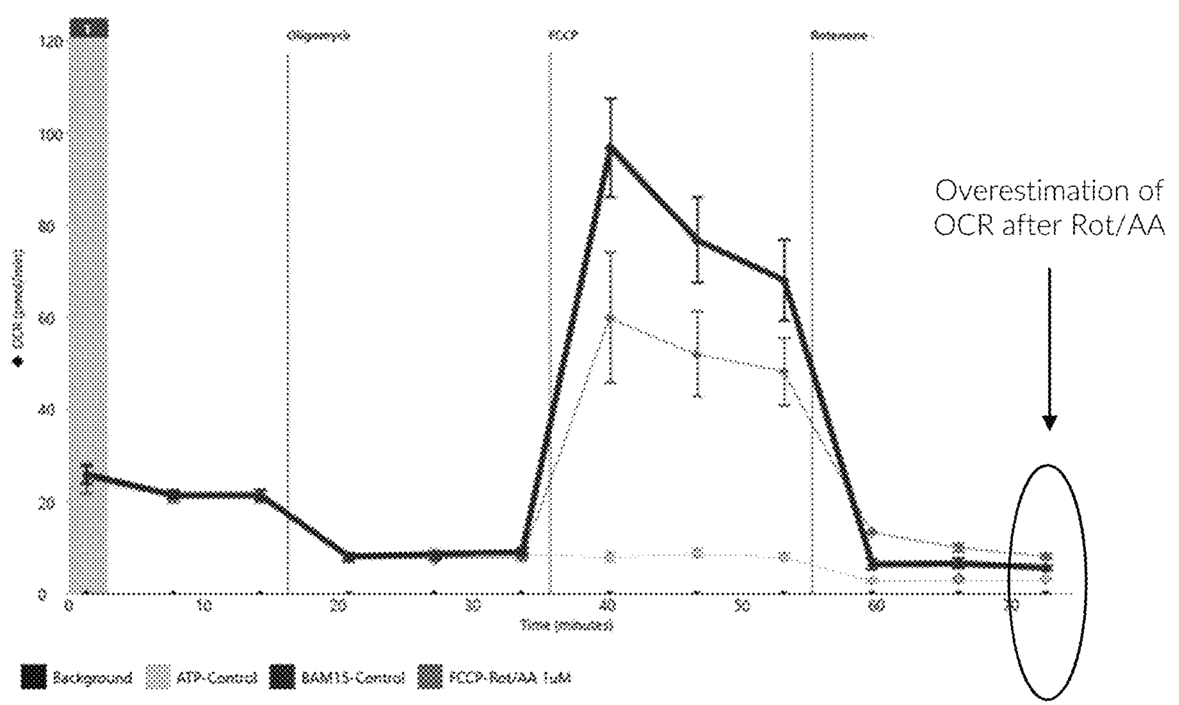
Figure 3C:
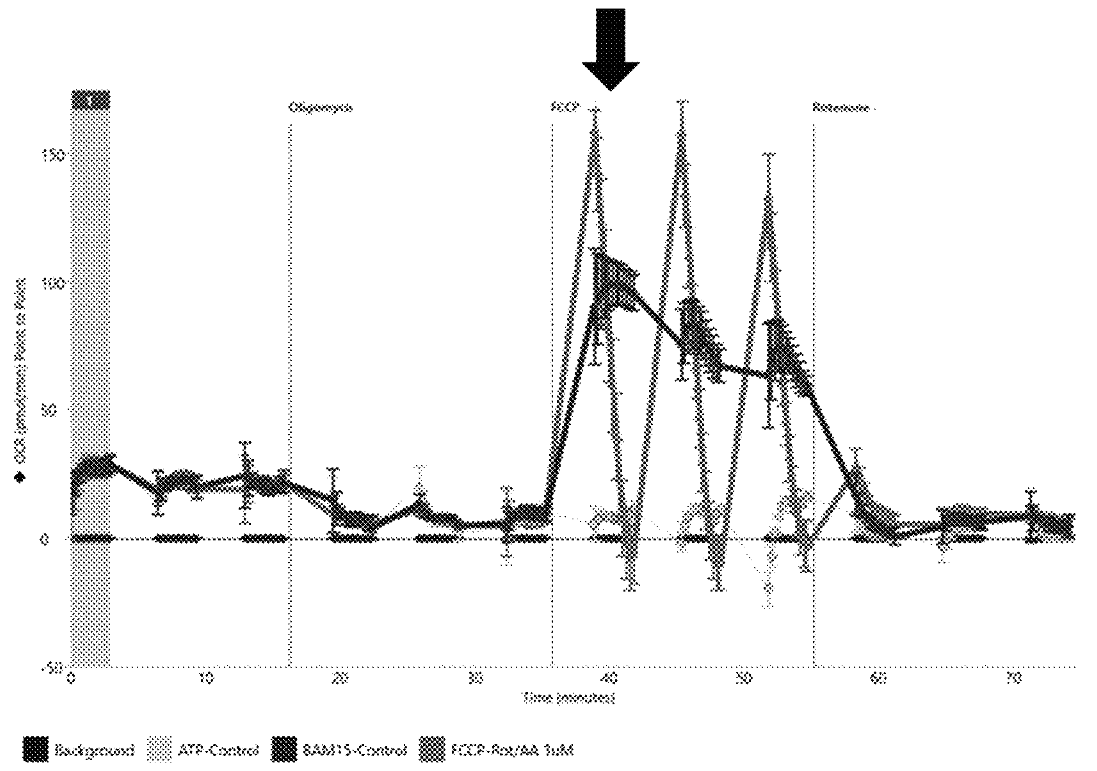

BAM15 was tested as a possible alternative to FCCP when measuring OCR in immune cells. The metabolic profiling of T cells was measured with oligomycin, either FCCP or BAM15, and Rotenone+antimycin A. When the maximal respiration was assayed with the addition of either FCCP or BAM15, the BAM15 induced a more robust measurement and provided an uncoupled response that was more stable during the 3 minutes of measurement time (FIGS. 3A, 3C) with minor overestimation of OCR after Rot/AA injection (FIG. 3B).

Figure 4A:
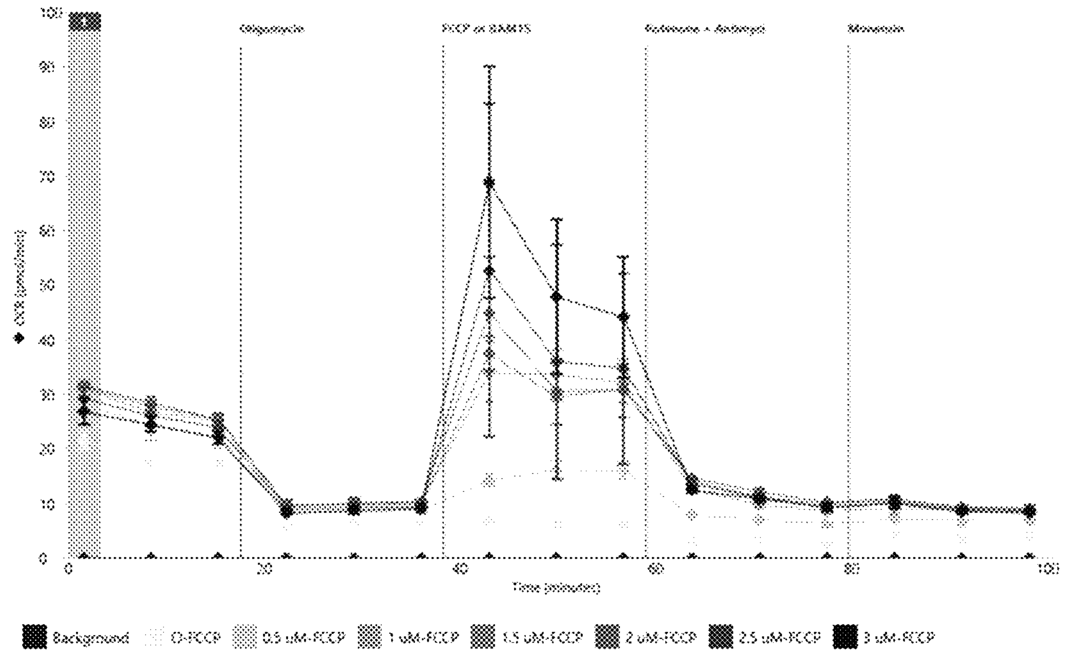
FIG. 4A-4D are graphs measuring OCR in Human Peripheral Blood CD4+ T cells (Stem Cell Technologies, Cat. No. 70026) and Human Peripheral Blood CD8+ T cell (Stem Cell Technologies, Cat. No. 70027 in response to titration of FCCP or BAM15. FCCP and BAM15 were tested at concentrations of 0.5 μM, 1 μM, 1.5 μM, 2 μM, 2.5 μM, or 3 μM in Human PB CD4+ T cells (FIGS. 4A-4B). FCCP and BAM15 were tested at the concentration of 2.5 μM in Human PB CD4+ T cells (FIG. 4C). FCCP and BAM15 were tested at the concentration of 3 μM and 2.5 μM, respectively, in Human PB CD8+ T cells (FIG. 4D).
Figure 4B:
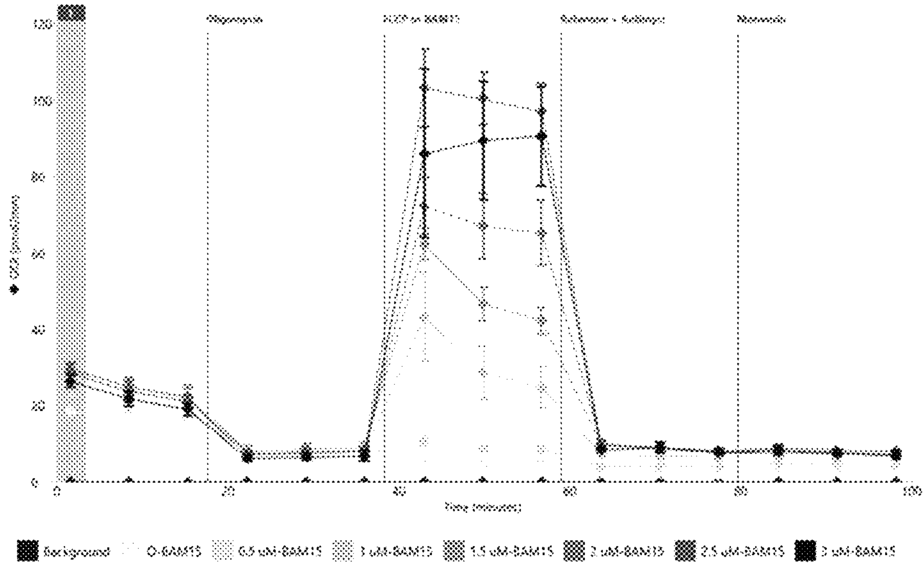
Figure 4C:
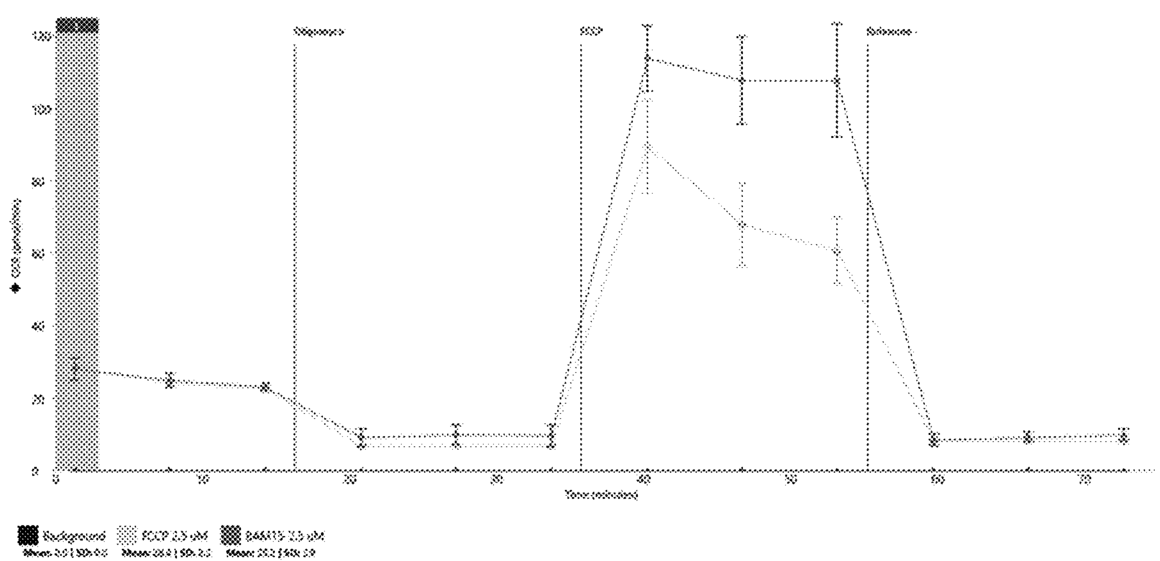
Figure 4D:
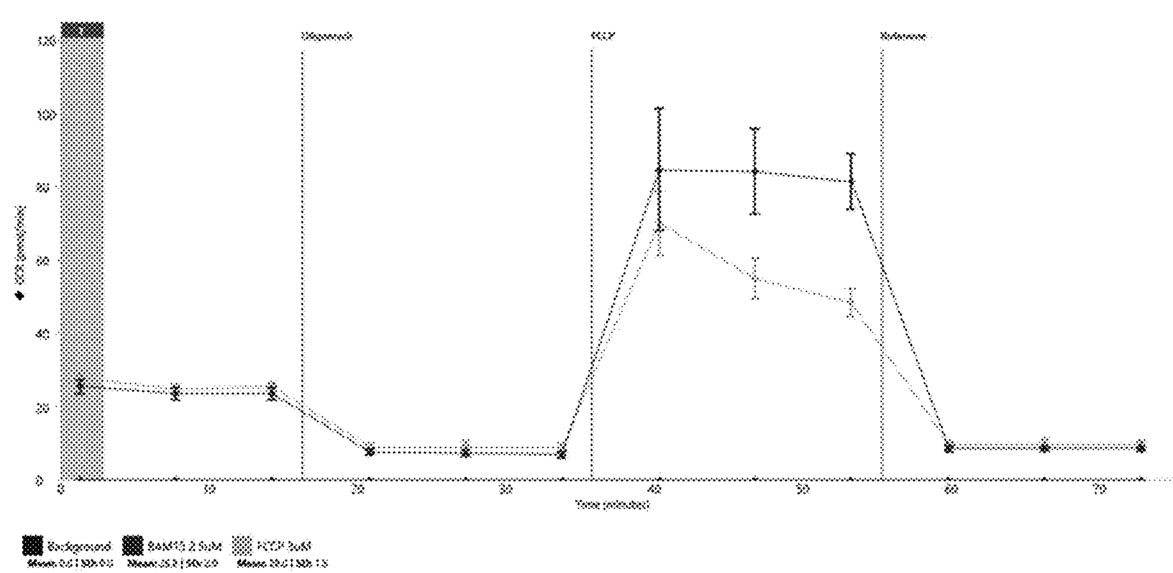

The maximal respiration was also tested in naïve CD4 and CD8 T cells with BAM15 and FCCP. FCCP or BAM15 concentrations were tested at different concentrations. The assays were performed with 0.5 μM, 1 μM, 1.5 μM, 2 μM, 2.5 μM, or 3 μM FCCP or BAM15 on naïve CD4+ T cells. The maximal respiration with the T cells tested with FCCP was not as robust nor was there an increase in a dose-dependent manner (FIG. 4A) as there was with BAM15 (FIG. 4B). Next, naïve CD4+ T cells were assayed using either FCCP or BAM15 at a concentration of 2.5 μM, and naïve CD8+ T cells were assayed using either FCCP at a concentration of 3.0 μM and BAM15 at a concentration of 2.5 μM. In both the naïve CD4+ and CD8+ T cells, a more consistent and more robust maximal respiration was measured with BAM15 (FIG. 4C-4D).

Figure 5A:
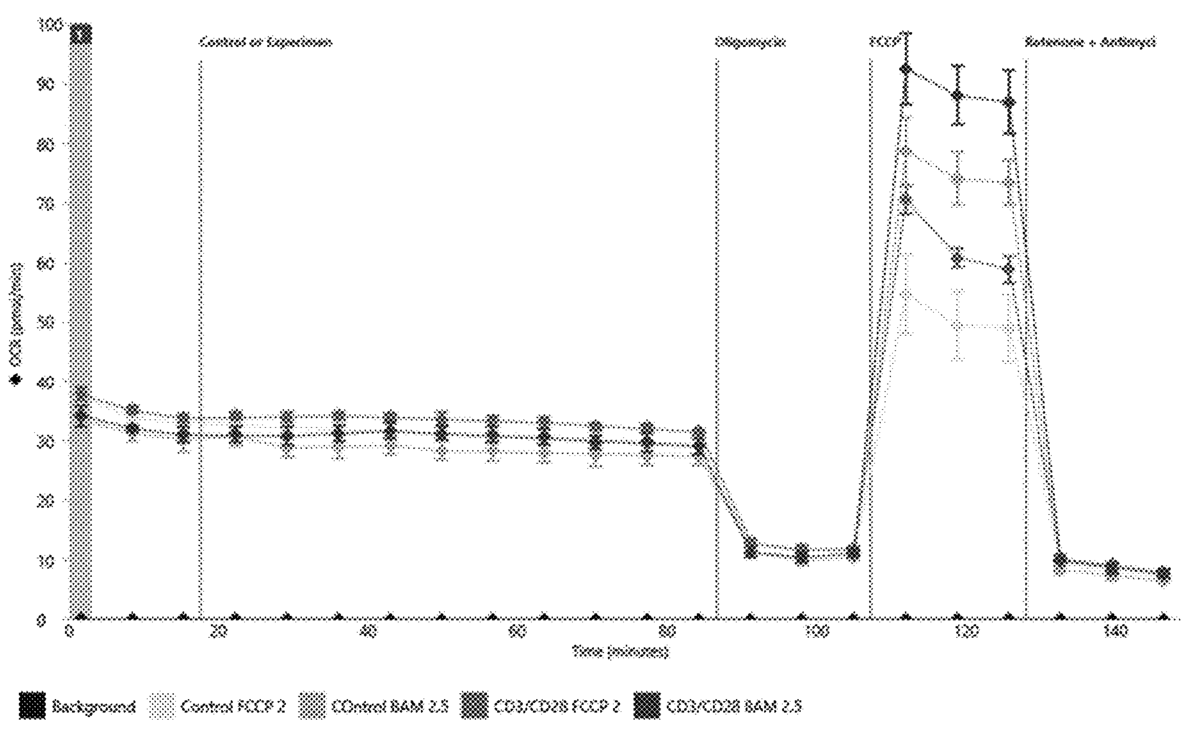
FIG. 5A-5B depict graphs of metabolic profiling performed on mouse CD8+ T cells isolated from spleen, either control or activated with CD3/CD28 antibodies conjugated to Dynabeads (Thermo Fisher, Cat. No. 11453D), using either 2.5 μM FCCP or 2.5 μM BAM15. Injections with oligomycin, FCCP or BAM15, and rotenone+antimycin A are indicated with the green lines and text. The OCR (pmol/min.
Figure 5B:
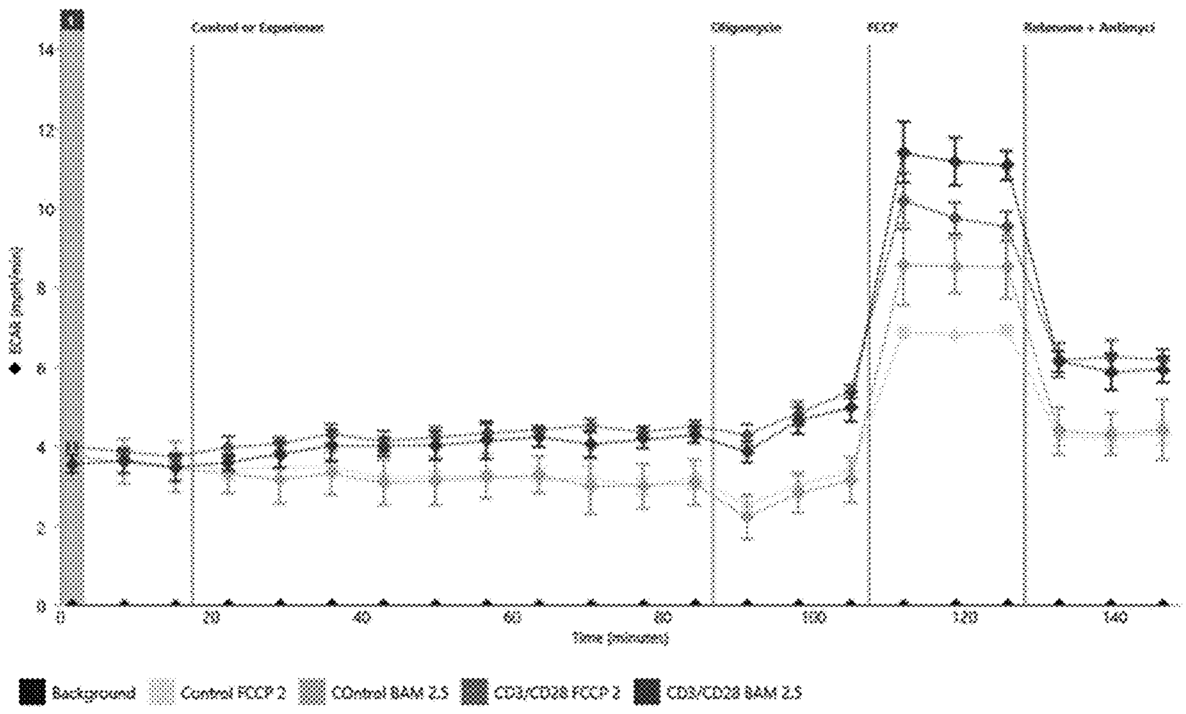

Next, the metabolic profile of naïve mouse CD8+ T cells that were stimulated with CD3/CD28 was assayed with pre-optimized concentrations of FCCP and BAM15 (2 μM and 2.5 μM, respectively in this instance of) (n=3). When the OCR and ECAR were plotted, the maximal respiration in both the control T cells and stimulated T cells was more robust following the addition of BAM15 compared to when FCCP was added to the assay (FIGS. 5A-5B). These studies demonstrated that BAM15 also minimized the need of uncoupler titration in each sample test.

Example 2: Calculation of Complete Bioenergetic Profile from a Single Assay

Figure 6:
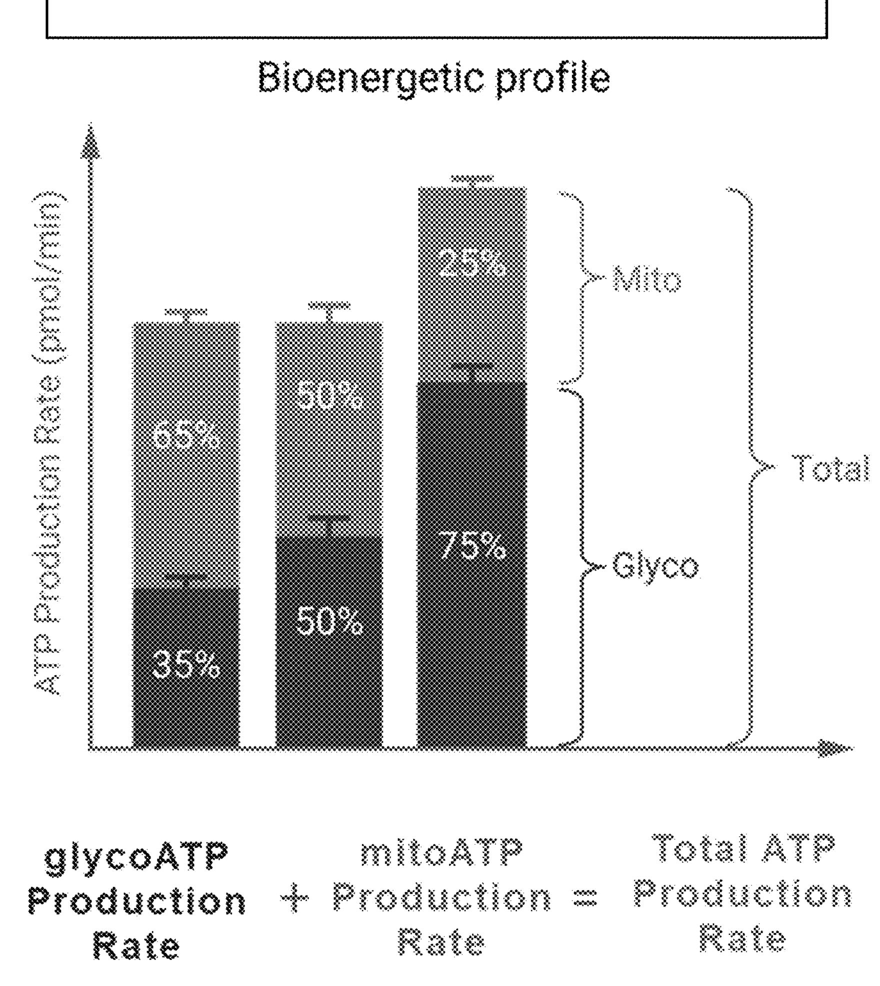
FIG. 6 illustrates how basal bioenergetic poise can be measured in live cells using the OCR (respiration) and ECAR (glycolysis) values. These values can be used to calculate the total ATP production rate (pmol/min).

The complete bioenergetic profile (the amount of ATP being generated by the cell) of live cells is calculated by measuring the bioenergetic poise (FIG. 6) and the bioenergetic reserve capacity (FIGS. 7 and 8). The bioenergetic poise is calculated as the proportion of ATP generated by glycolysis to oxidative phosphorylation, while the bioenergetic reserve capacity or the bioenergetic capacity is calculated as the level of increase in glycolytic and mitochondrial activity that the cell can affect in response to an increase in energy demand.

Figure 7A:
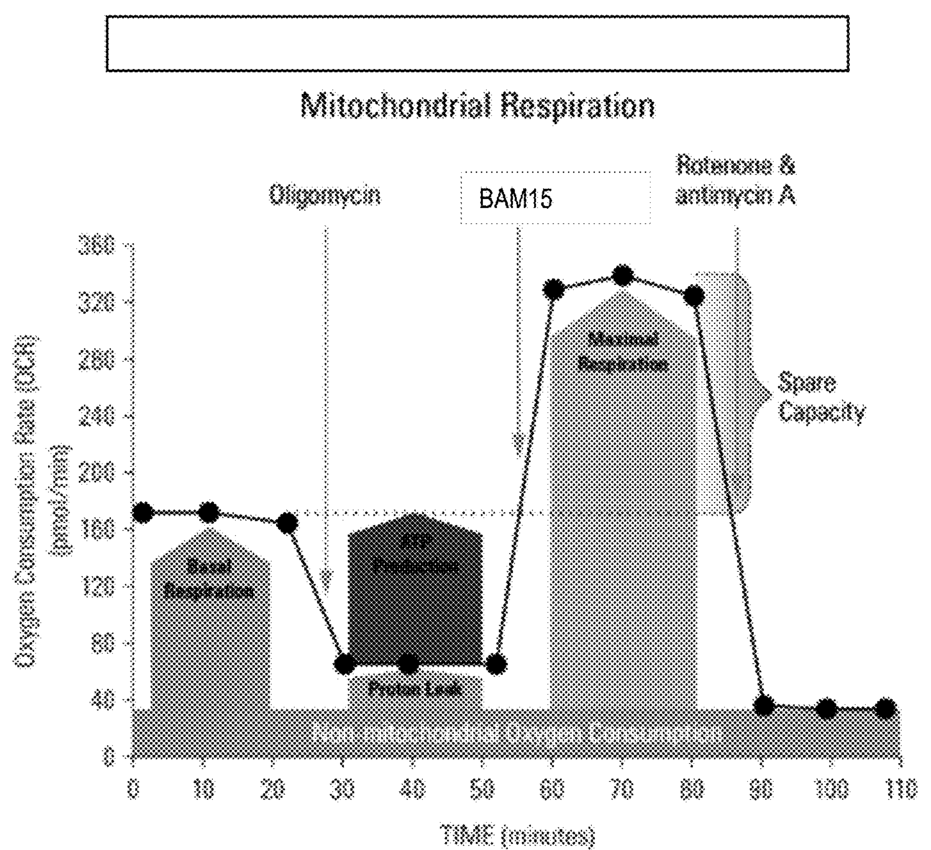
FIG. 7A-7B illustrate how the metabolic profiling assay can be used to calculate the spare mitochondrial ATP production rate (pmol/min/$1\times10^5$ cells; y-axis). The spare mitochondrial ATP production rate can be calculated as the difference between the maximal OCR after BAM15 injection and the last measurement of OCR prior to the first injection. Aerobic reserve capacity can be expressed in units of Rates of ATP production by multiplying by P/O Ratio.
Figure 7B:
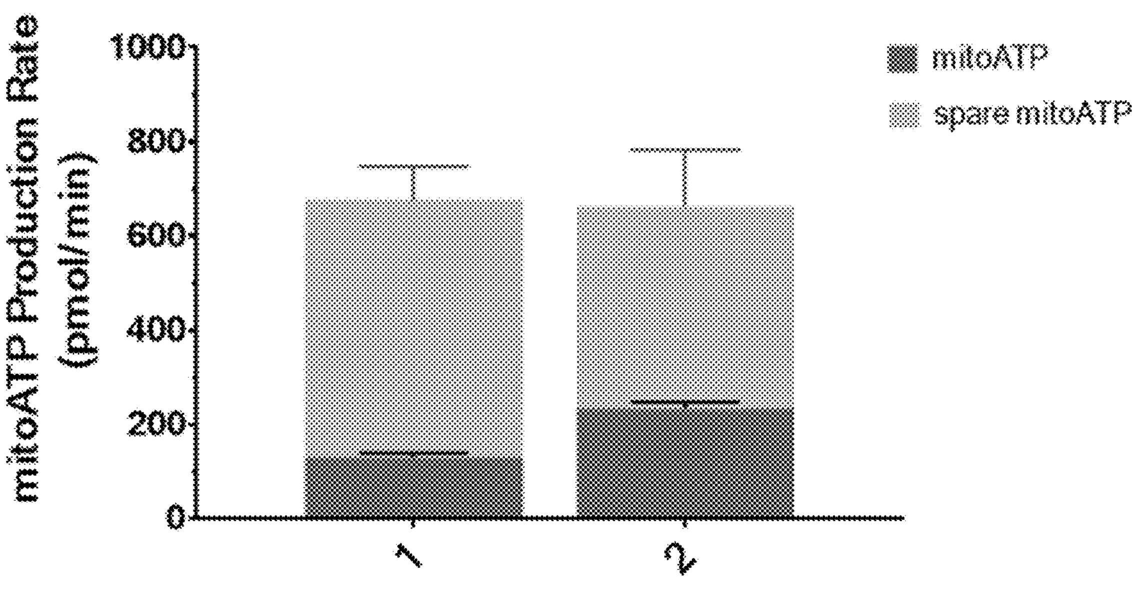

Reserve aerobic capacity can be measured in live cells obtaining the "theoretical maximal value." This assumes that ATP yield per oxygen is the same in uncoupled conditions compared to coupled conditions. The reserve aerobic capacity is calculated as the difference between the maximal measurement of oxygen consumption rate after BAM15 injection and the basal respiration. In this instance itis expressed as rates of ATP production using a P/O ratio of 2.75 (FIGS. 7A-7B).

Figure 8A:
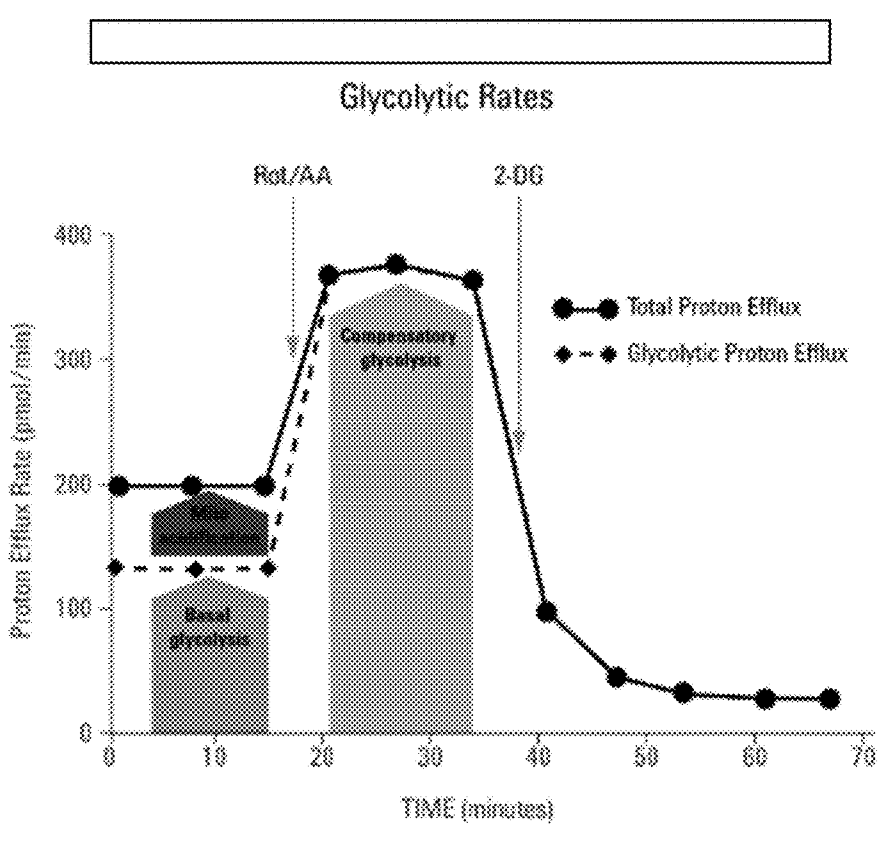
FIG. 8A-8B illustrate how the metabolic profiling assay can be used to obtain the glycolytic rate profile and calculate the spare glycolytic ATP production rate (pmol/min/$1\times10^5$ cells; y-axis).
Figure 8B:
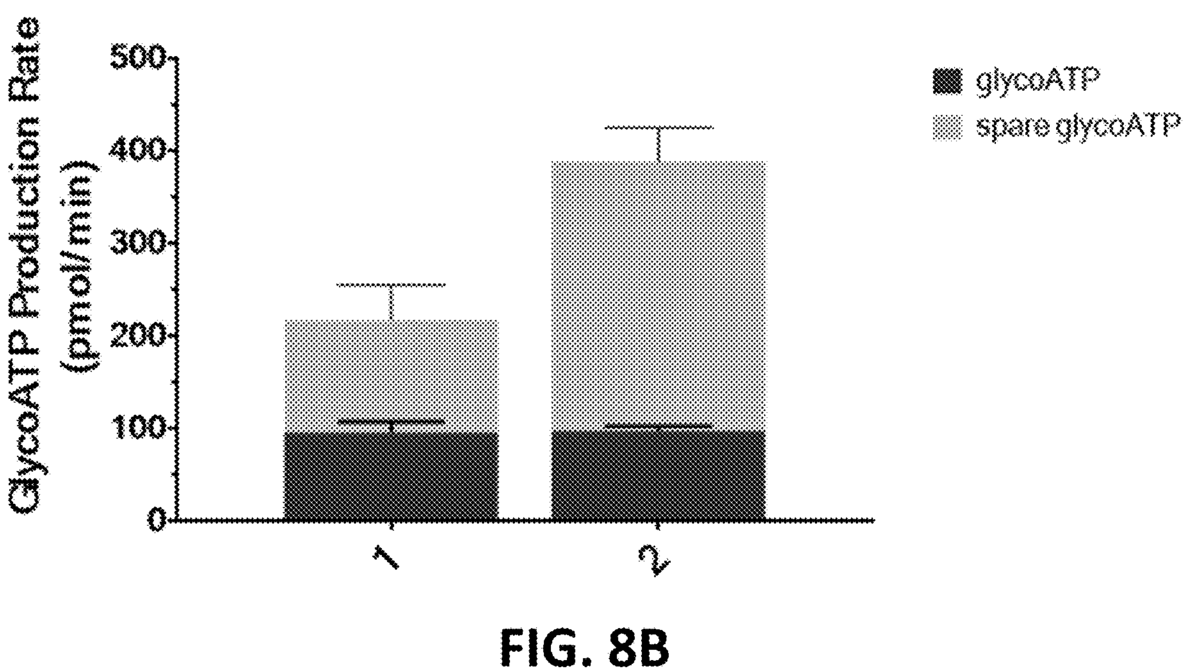
Figure 9A:
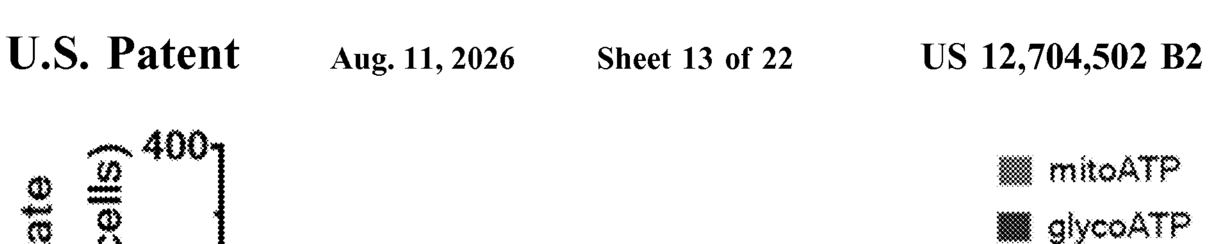
FIG. 9A-9E depict graphs of the basal ATP production rate and metabolic poise (FIG. 9A), the glycolytic ATP production rate (glycolytic bioenergetic capacity) (FIG. 9B), the total ATP production rate (bioenergetic capacity) (FIG. 9C), the mitochondrial ATP production rate (mitochondrial bioenergetic capacity) (FIG. 9D), and the spare respiratory capacity (FIG. 9E) in Human Peripheral Blood Pan T cells (STEMCELL Technologies, Cat. No. 200-0170) activated and expanded for 7 days under different culture medium conditions. Human Peripheral Blood Pan T cells were activated with Dynabeads Human Activator CD3/CD28 in Immunocult XF T Cell Expansion Medium (Stem Cell Technologies, Cat. No. 10981) and culture at 37 C in a 5% CO2 incubator. 2 Days after activation, Dynabeads were removed and cells were split in 4 groups and resuspended at $1\times10^6$ cells/mL in Immunocult XF Medium (Medium B) supplanted with IL-2 (300 U/mL), Medium B supplemented with IL-15 (10 ng/mL), RPMI supplemented with 2 mM glutamine and 10% FBS (Medium A) and IL-2 (300 U/mL) or Medium A supplemented with IL-15 (10 ng/mL).
Figure 9B:
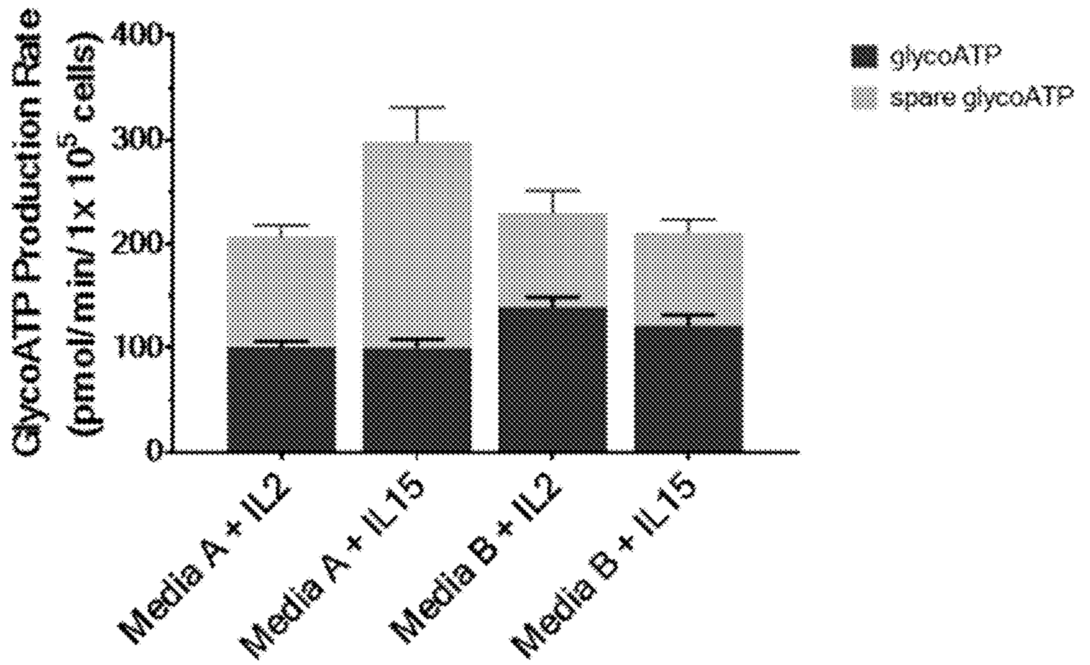
Figure 9C:
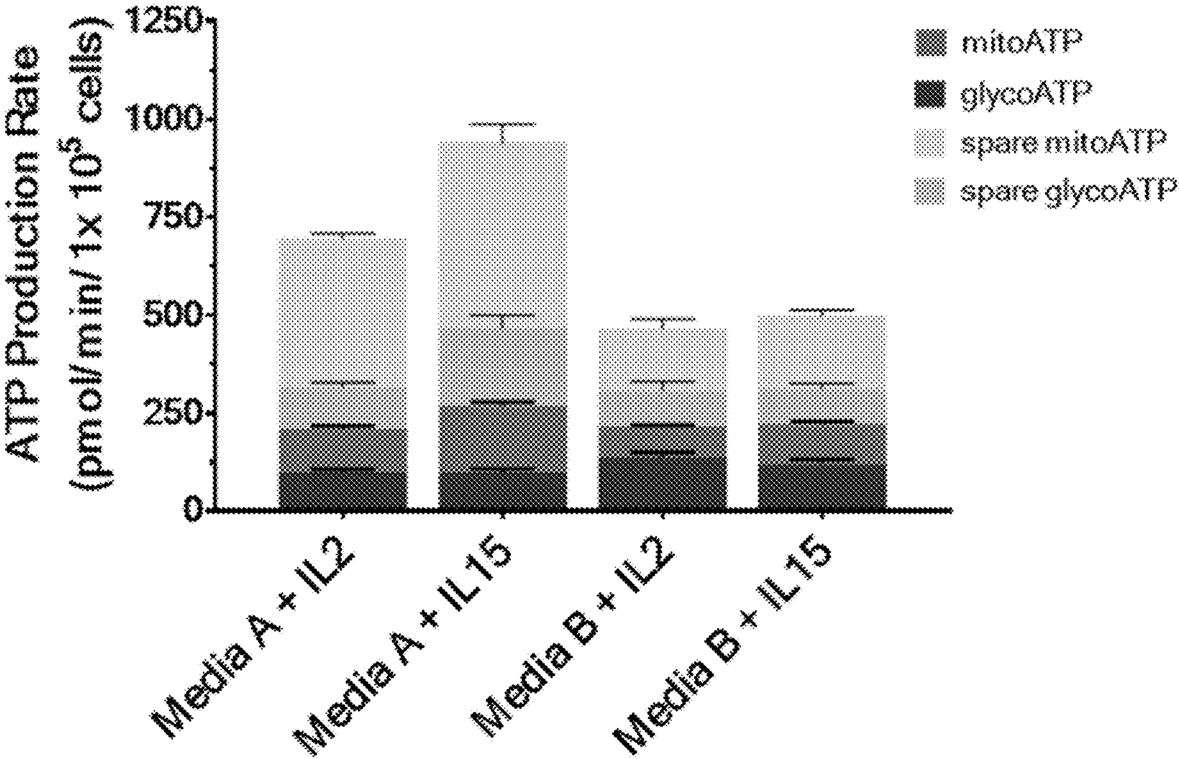
Figure 9D:
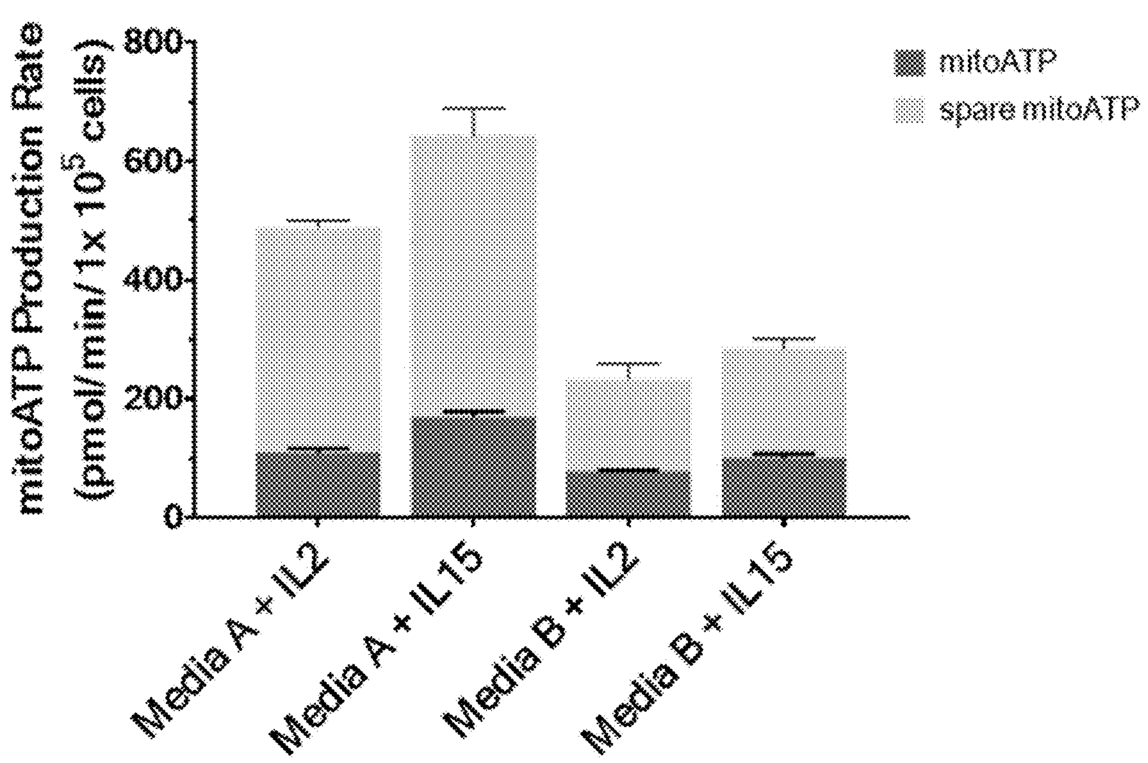
Figure 9E:
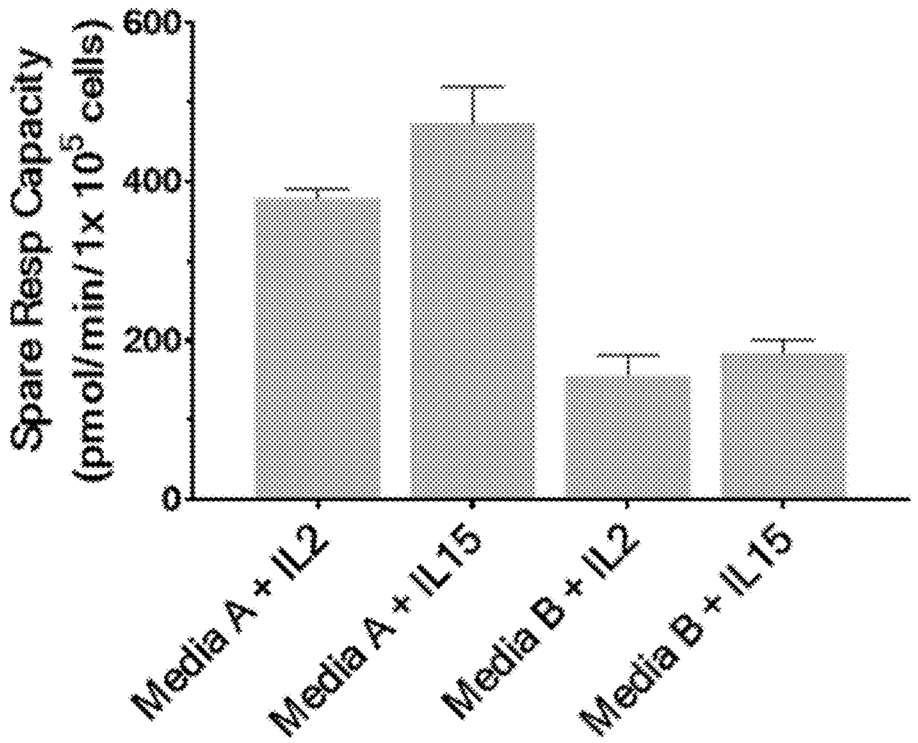
Figure 10:
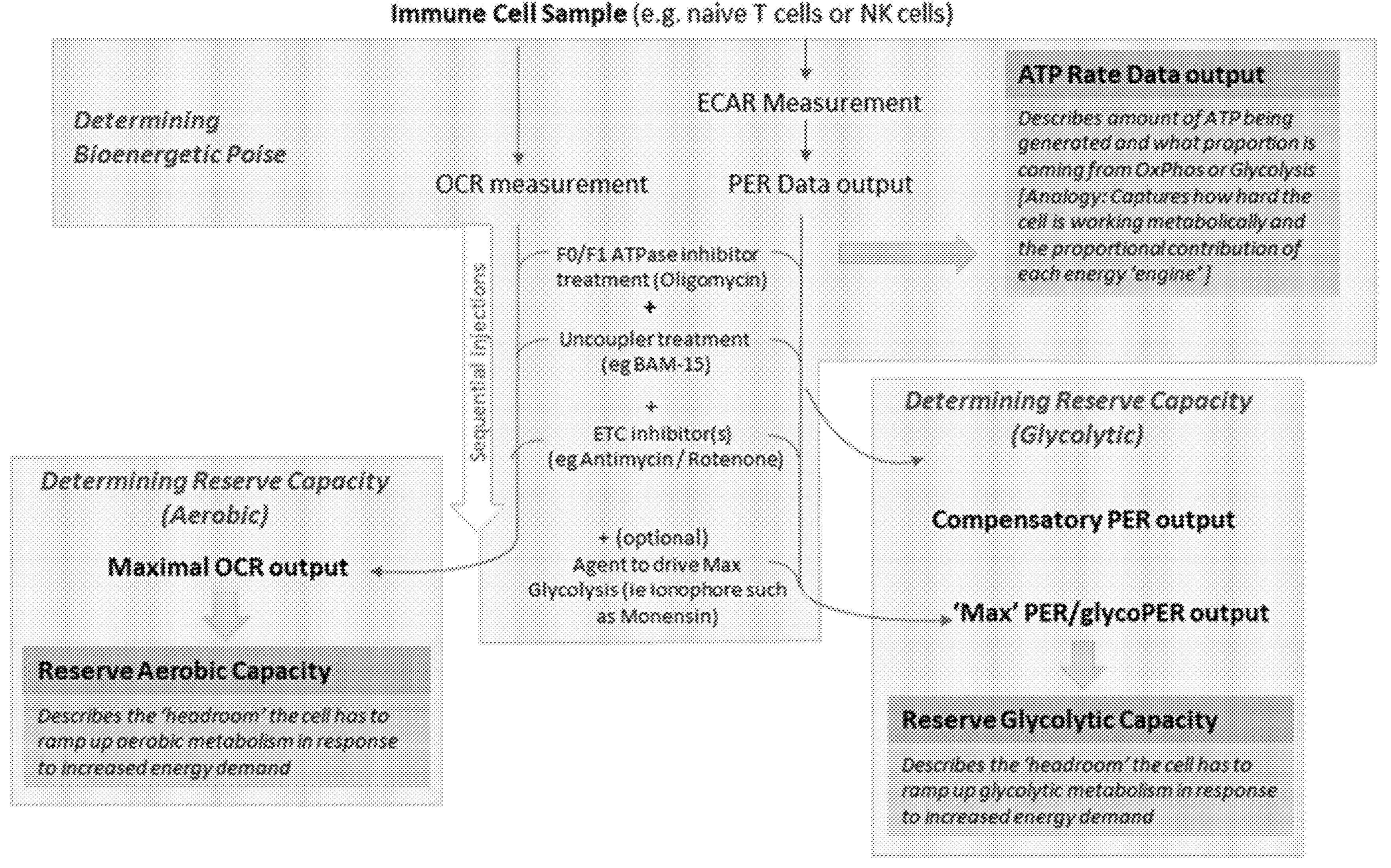
FIG. 10 depicts an exemplary workflow of determining bioenergetic work, bioenergetic poise and bioenergetic capacity of a cell sample.

The compensatory glycolytic capacity or glycolytic reserve rate is the glycolytic rate when mitochondrial activity is blocked. This gives an indication of the "spare" glycolytic activity available. In some cases, this can be higher, and the addition of monensin can provide a confirmation of the maximal glycolytic capacity measurement (FIGS. 8A-8B).

The total bioenergetic capacity of expanded human Pan-T cells was measured as described herein. Human Pan T-cells were expanded in two different culture medium (medium A or B) supplemented with 2 different interleukins IL-2 (300 U/mL) or IL-15 (10 ng/mL) reported to induce different T cell phenotypes (Medium A: RPMI containing 11 mM glucose and supplemented with 2 mM glutamine and 10% FBS; Medium B: Immunocult XF T Cell Expansion Medium, Stem Cell Technologies, Cat. No. 10981). The ATP production rate, the glycolytic ATP production rate, the mitochondrial ATP production rate, the spare glycolytic ATP production rate, the spare respiratory capacity, and the total bioenergetic capacity were calculated (FIGS. 9A-9E) by plating $1\times10^5$ Pan-T cells resuspended in XF RPMI pH 7.4 supplemented with 10 mM glucose, 2 mM glutamine and 1 mM pyruvate, in a PDL-coated plate and measuring OCR and PER before and after sequential injection of oligomycin A (1.5 μM), BAM15 (2.5 μM) and Rotenone/Antimycin A (0.5 μM each).

Example 3: Performance of Mitochondrial Uncouplers and calculation of Complete Bioenergetic Profile in NK Cells In this example, the performance of the mitochondrial uncouplers FCCP and BAM15 was assessed in human peripheral blood NK cells, as assayed by the addition of either FCCP or BAM15 and measurement of oxygen consumption rate (OCR), extracellular oxygen levels, and point to point OCR at various times over the course of the experiment. NK cells were cultured as described herein (e.g., in Example 1). NK cells were treated with FCCP or BAM15, and then assayed as described above, in accordance with the methods described herein (e.g., in Example 1).

Figure 11A:
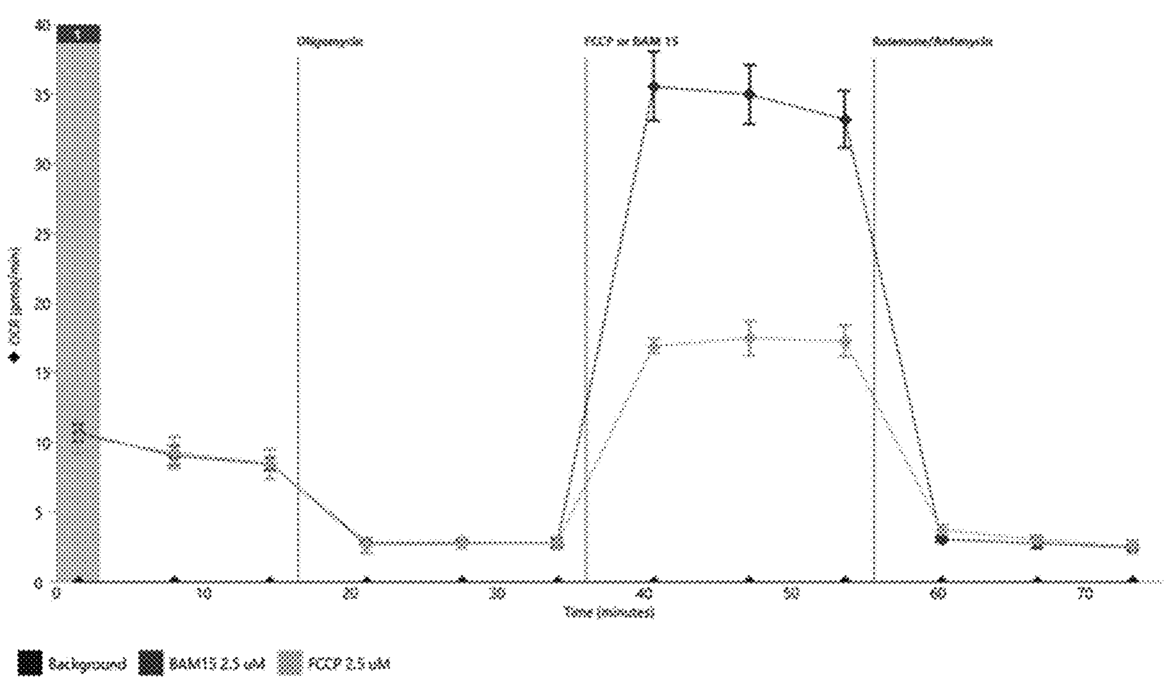
FIGS. 11A-11C are graphs for a metabolic profiling assay using 2.5 μM FCCP to measure uncoupled respiration in Human Peripheral Blood NK cells (Stem Cell Technologies, Cat. No. 70036). Oxygen Consumption Rate (OCR) (FIG. 11A), Extracellular oxygen levels (FIG. 11B), and OCR (point to point) (FIG. 11C) are shown.
Figure 11B:
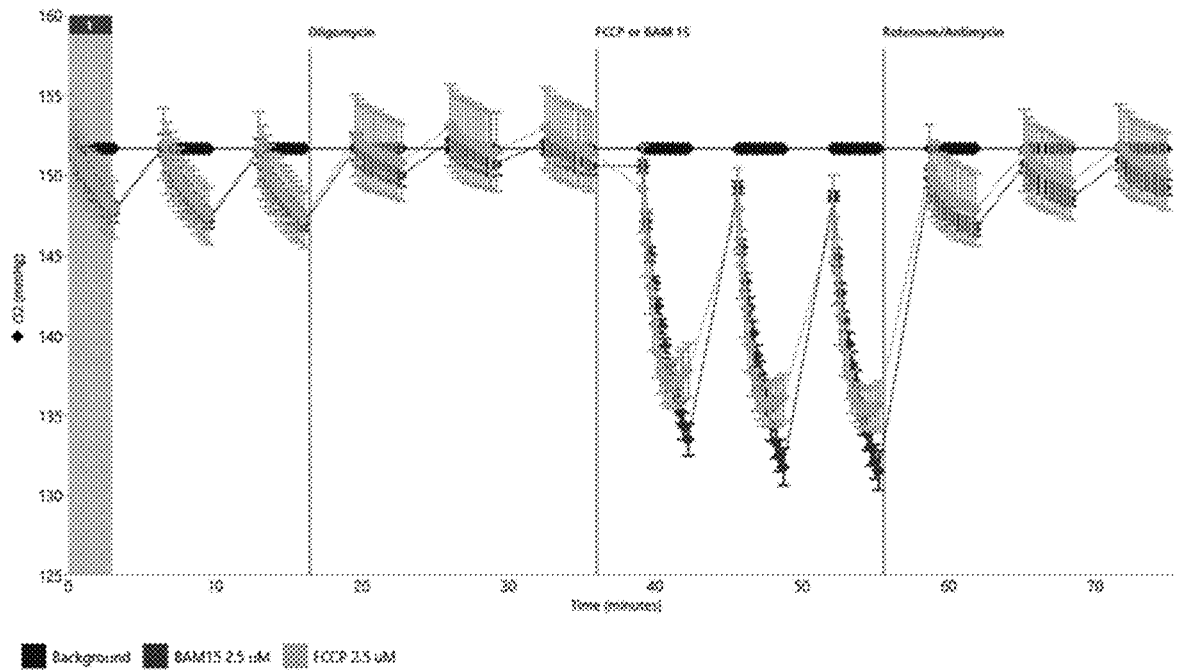
Figure 11C:
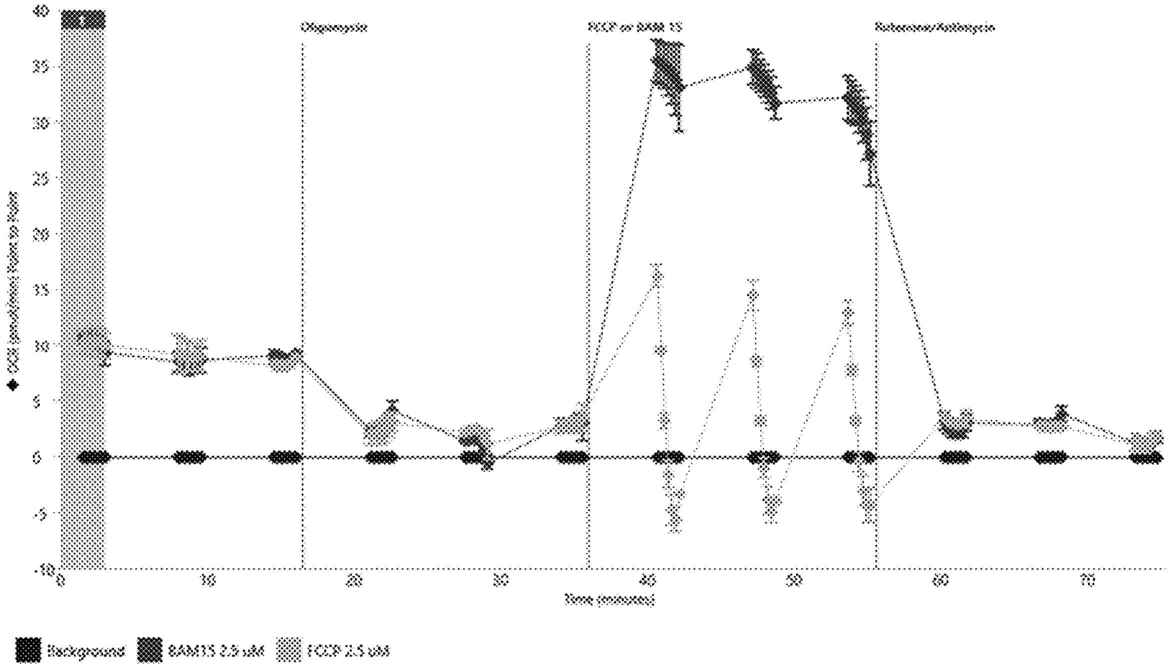
Figure 12A:
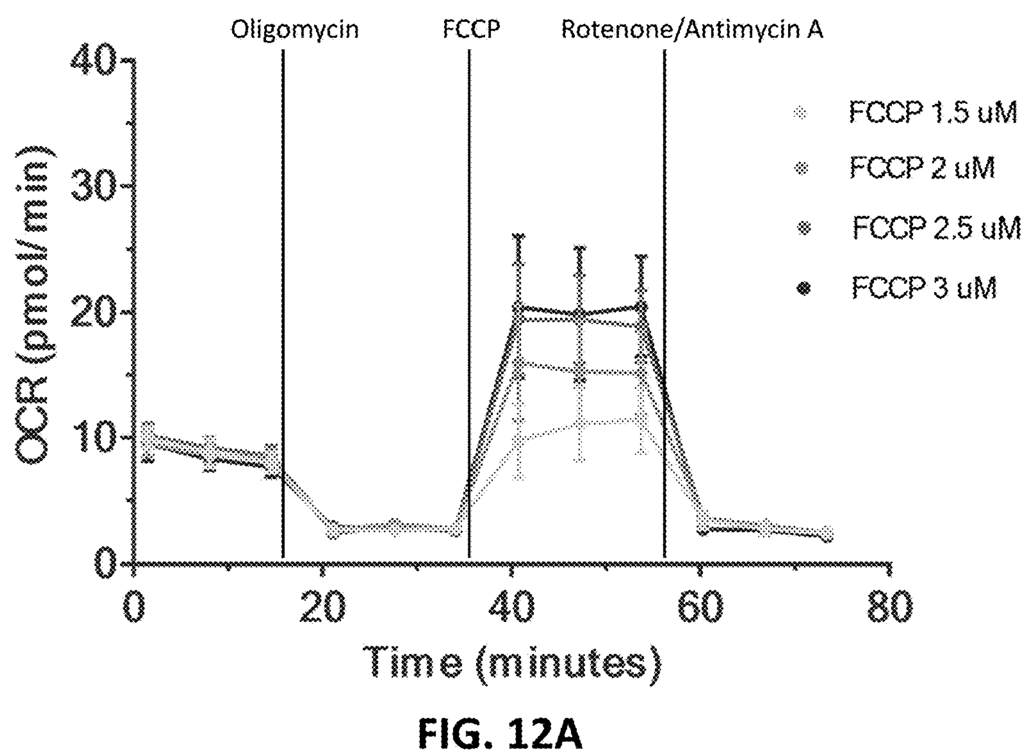
FIGS. 12A-12B are graphs measuring OCR in Human Peripheral Blood NK cells (Stem Cell Technologies, Cat. No. 70036) in response to titration of FCCP or BAM15. FCCP and BAM15 were tested at concentrations of 1 μM, 2 μM, 2.5 μM, or 3 μM in Human PB NK cells (FIGS. 12A-12B).
Figure 12B:
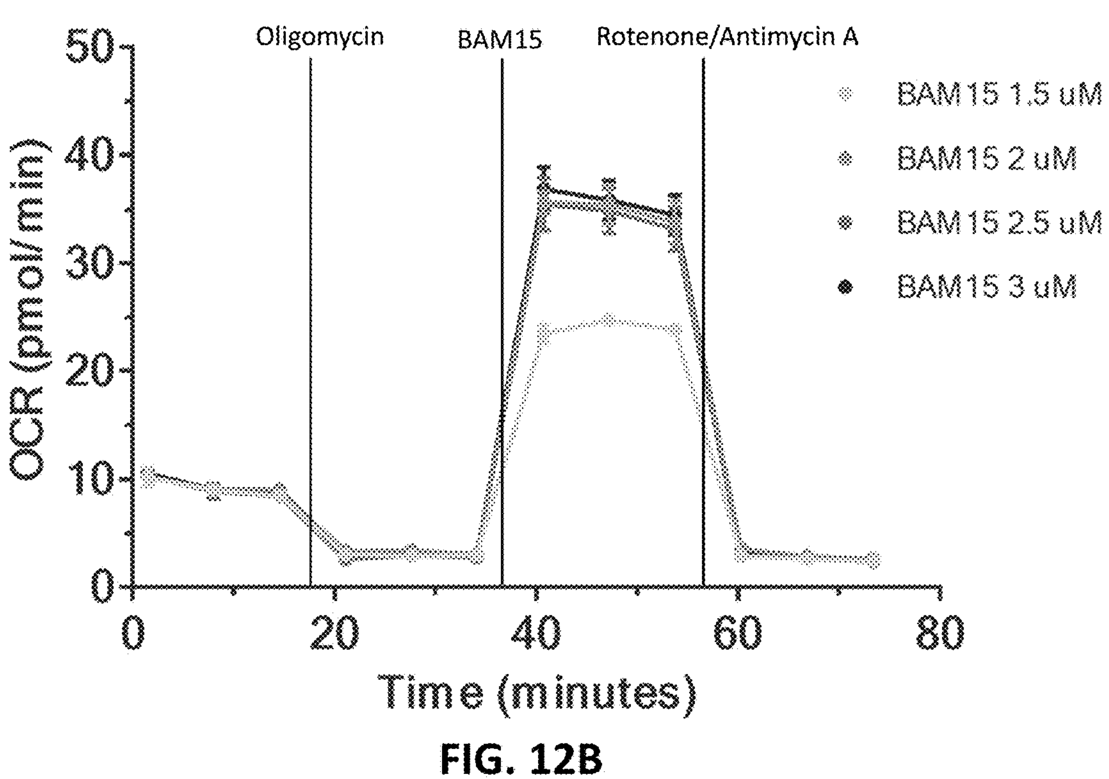
Figure 13A:
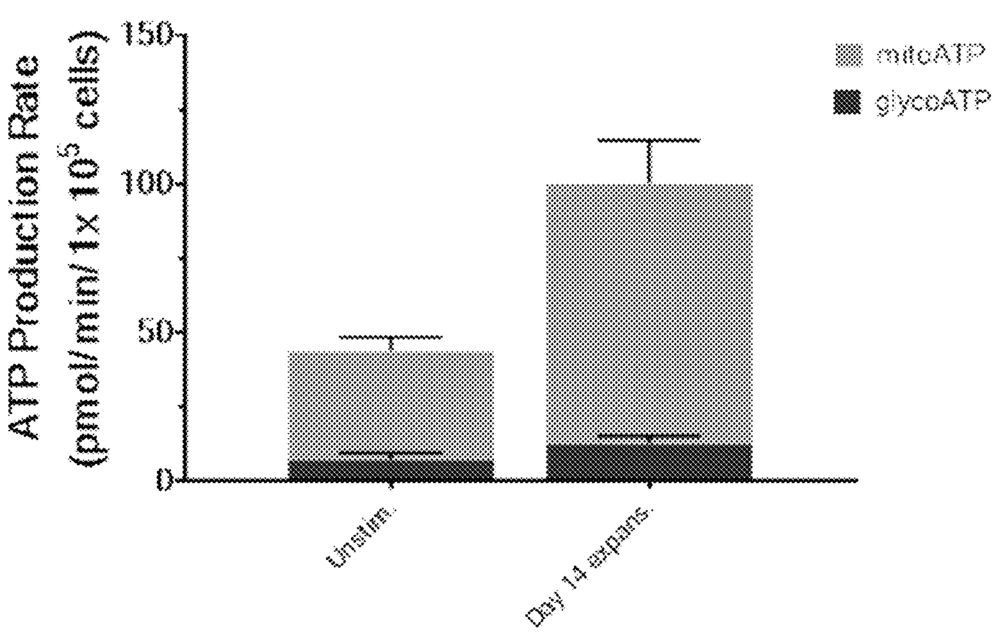
FIGS. 13A-13E depict graphs of the basal ATP production rate and metabolic poise (FIG. 13A), the glycolytic ATP production rate (glycolytic bioenergetic capacity) (FIG. 13B), the total ATP production rate (bioenergetic capacity) (FIG. 13C), the mitochondrial ATP production rate (mitochondrial bioenergetic capacity) (FIG. 13D), and the spare respiratory capacity (FIG. 13E) in Human Peripheral Blood NK cells (Stem Cell Technologies, Cat. No. 70036) unstimulated or stimulated and expanded for 14 days in RPMI supplemented with 2 mM glutamine, 10% FBS and IL-2 (1000 U/mL) and 10% FBS.
Figure 13B:
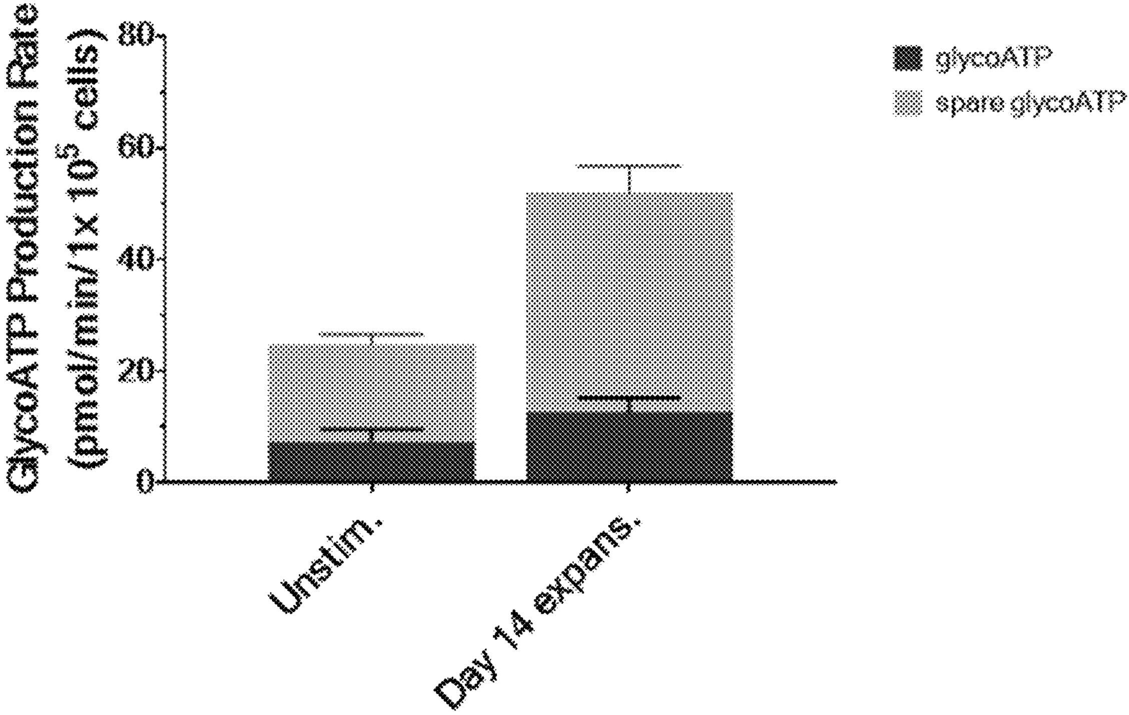
Figure 13C:
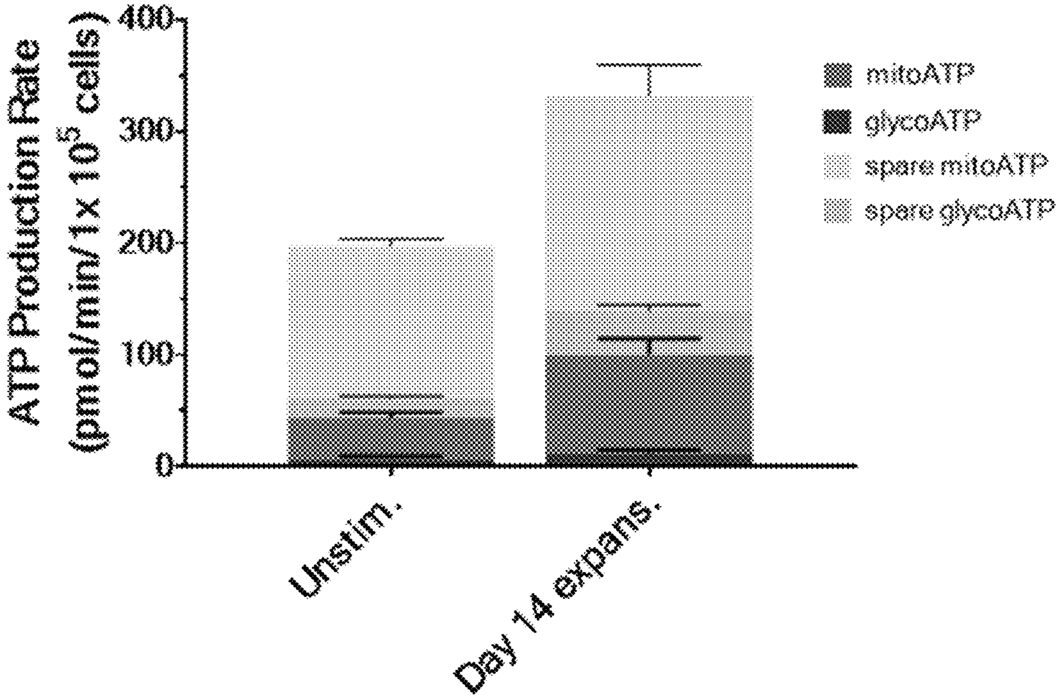
Figure 13D:
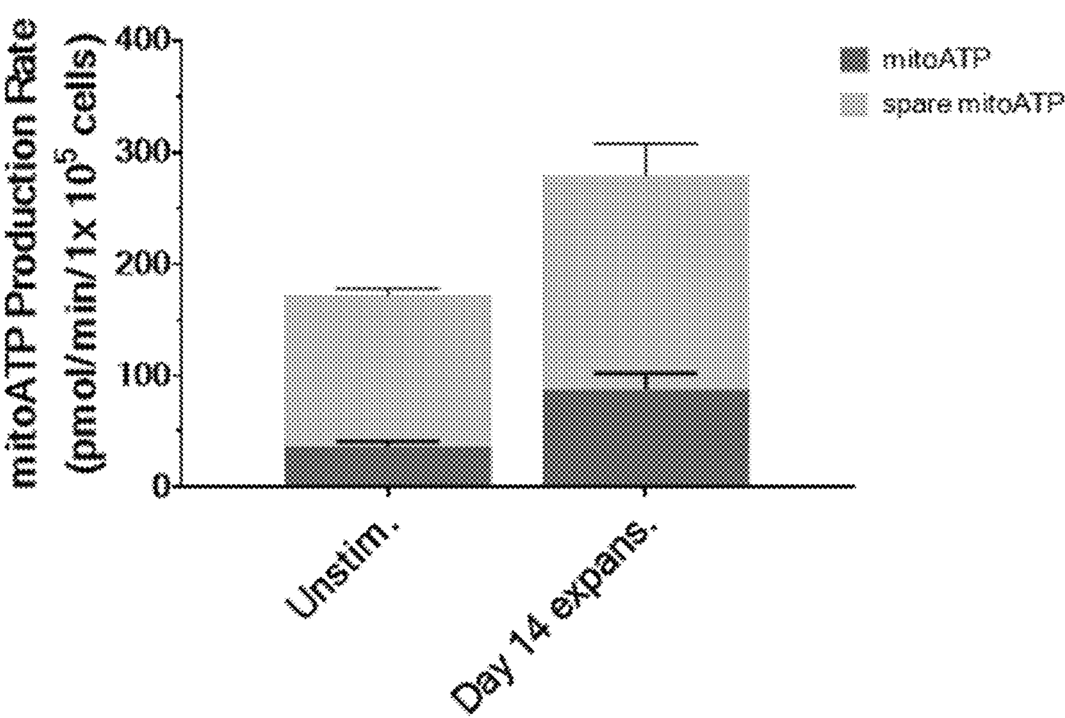
Figure 13E:
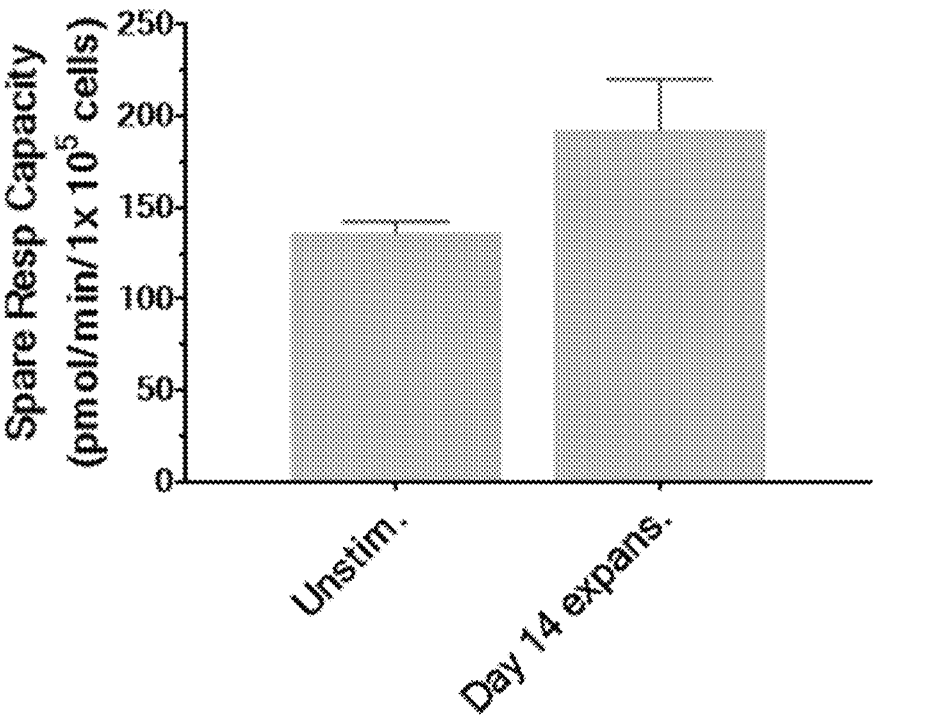

Treatment with BAM15 resulted in a significantly greater increase in OCR compared to treatment with FCCP (FIG. 11A). BAM15 also induced a more robust measurement and provided an uncoupled response that was more stable during the 3 minutes of measurement (FIGS. 11B-11C). The maximal respiration was also tested at different FCCP and BAM15 concentrations. The assays were performed with 1.5 μM, 2 μM, 2.5 μM, or 3 μM FCCP or BAM15. The maximal respiration obtained with FCCP was not as robust as there was with BAM15 (FIGS. 12A and 12B) showing the BAM15 provides higher maximal respiration, and also minimized the need of uncoupler titration in each sample test.

The bioenergetic profile of unstimulated human peripheral blood NK cells or NK cells from the same donor stimulated with IL-2 and expanded in cell culture medium during 14 days was also determined. As described in Example 2, bioenergetic poise was calculated as the proportion of ATP generated by glycolysis to oxidative phosphorylation, while the reserve capacity or the bioenergetic capacity was calculated as the level of increase in glycolytic and mitochondrial activity that the cell can affect in response to an increase in energy demand.

The total bioenergetic capacity of unstimulated or expanded human peripheral blood NK cells (Stem Cell Technologies, Cat. No. 70036) was measured as described herein. NK cells were thawed and resuspended at $1\times10^6$ cells/mL and incubated overnight in RPMI supplemented with 2 mM glutamine, 10% FBS 37C in a 5% CO2 incubator or stimulated with IL-2 (1000 U/mL) and cultured during 14 days adjusting every 3 days cell density to $1\times10^6$ cells/mL. After the indicated incubation period, cells were washed and resuspended in XF RPMI Assay Medium (Agilent Technologies, Cat. No. 103576-100) supplemented with 10 mM glucose, 2 mM Glutamine, and 1 mM pyruvate, and cells were assayed in the Seahorse XF Analyzer. The basal ATP production rate, the compensatory glycolytic capacity, the total bioenergetic capacity, the mitochondrial bioenergetic capacity, and the spare respiratory capacity were calculated. These studies demonstrated that after 14 days of expansion NK cells present a higher basal ATP production and bioenergetic capacity mainly sustained by an increase in mitochondrial ATP production and spare respiratory capacity. (FIGS. 13A-13E)

These results demonstrate the impact of the expansion conditions on the metabolic profile of immune cells and its potential utility for designing and validating the production of more efficient immune cell therapies.

What is claimed is:

1. A method of evaluating the bioenergetic poise and bioenergetic capacity of a cell sample, comprising:

acquiring a reference value for oxygen consumption ($VOC_{Ref}$);

acquiring a reference value for proton efflux ($VPE_{Ref}$);

contacting the cell sample with an Adenosine Triphosphate (ATP) synthase inhibitor, a mitochondrial uncoupling agent, and an electron transport chain (ETC) inhibitor, sequentially, each contacting forming a reaction mixture, wherein:

(i) a first value for oxygen consumption and a first value for proton efflux are acquired after the ATP synthase inhibitor is contacted with the cell sample;

(ii) a second value for oxygen consumption and a second value for proton efflux are acquired after the mitochondrial uncoupling agent is contacted with the cell sample; and (iii) a third value for oxygen consumption and a third value for proton efflux are acquired after the ETC inhibitor is contacted with the cell sample;

acquiring a value for oxygen consumption for each reaction mixture ($VOC_{Mix}$); and acquiring a value for proton efflux for each reaction mixture ($VPE_{Mix}$), thereby evaluating the bioenergetic poise and bioenergetic capacity of the cell sample.

2. The method of claim 1, wherein:

(i) a value for oxygen consumption and a value for proton efflux are acquired after the ATP synthase inhibitor is contacted with the cell sample;

(ii) a value for oxygen consumption and a value for proton efflux are acquired after the mitochondrial uncoupling agent is contacted with the cell sample;

(iii) a value for oxygen consumption and a value for proton efflux are acquired after the ETC inhibitor is contacted with the cell sample;

(iv) the $VOC_{Ref}$ comprises a basal or initial value for oxygen consumption for the cell sample, including a value based on a measurement of oxygen consumption for the cell sample made prior to formation of a reaction mixture;

(v) acquiring a $VOC_{Ref}$ comprises determining a basal or initial OCR for the cell sample;

(vi) determining the basal or initial OCR for the cell sample comprises sensing a metabolite consumed from medium;

(vii) the $VPE_{Ref}$ comprises a basal or initial value for proton efflux for the cell sample, including a value based on a measurement of proton efflux for the cell sample made prior to formation of the reaction mixture;

(viii) the proton efflux is measured by proton efflux rate (PER);

(ix) an extracellular acidification rate (ECAR) is measured to produce a value for proton efflux;

(x) acquiring a $VPE_{Ref}$ comprises determining a basal or initial PER for the cell sample, optionally wherein determining the basal or initial PER for the cell sample comprises sensing a metabolite or a cell constituent disposed in the medium;

(xi) the $VOC_{Ref}$ and the $VPE_{Ref}$ are based on measurements of oxygen consumption and proton efflux initiated within 10 hours of one another;

(xii) the $VOC_{Ref}$ and the $VPE_{Ref}$ are based on measurements of oxygen consumption and proton efflux initiated within a time period suitable for rapid instrument data acquisition within 800 milliseconds;

(xiv) the $VOC_{Ref}$ and the $VPE_{Ref}$ are based on measurements of oxygen consumption and proton efflux initiated within a time period suitable for a long-term end-point measurement, within 9 hours;

(xv) the $VOC_{Ref}$ and the $VPE_{Ref}$ are based on measurements of oxygen consumption and proton efflux initiated sequentially;

(xvi) the $VOC_{Ref}$ and the $VPE_{Ref}$ are based on measurements of oxygen consumption and proton efflux initiated substantially simultaneously;

(xvii) contacting the cell sample with the ATP synthase inhibitor, the mitochondrial uncoupling agent, and the ETC inhibitor comprises introducing the ATP synthase inhibitor, the mitochondrial uncoupling agent, and the ETC inhibitor, sequentially, partly simultaneously, or simultaneously, into a well or microchamber disposed with the cell sample; or (xviii) the ATP synthase inhibitor, the mitochondrial uncoupling agent, and the ETC inhibitor are contacted with the cell sample sequentially.

3. The method of claim 1, wherein oxygen consumption is:

(i) not determined in a sealed system, e.g., a system allows oxygen back diffusion or substantial oxygen back diffusion to the sample;

(ii) oxygen depletion in the sample corrected for oxygen back diffusion to the sample;

(iii) oxygen depletion without being corrected for oxygen back diffusion to the sample;

(iv) determined in a sealed system, e.g., a system that does not allow oxygen back diffusion or substantial oxygen back diffusion to the sample;

(v) equals, or substantially equals, to oxygen depletion in the sample;

(vi) determined directly or indirectly, e.g., inferred from a measured oxygen gradient, e.g., within a test well, or across a capillary, or by measuring oxygen at a preselected time point;

(vii) the $VOC_{Ref}$ comprises a basal or initial value for oxygen consumption for the cell sample, e.g., a value based on a measurement of oxygen consumption for the cell sample made prior to formation of a reaction mixture; and/or (viii) is measured (e.g., directly or indirectly) by oxygen consumption rate (OCR).

4. The method of claim 1, wherein the ATP synthase inhibitor, the mitochondrial uncoupling agent, and the ETC inhibitor are contacted with the cell sample in the order of (from first to last):

(a) the ATP synthase inhibitor, the mitochondrial uncoupling agent, the ETC inhibitor;

(b) the ATP synthase inhibitor, the ETC inhibitor, the mitochondrial uncoupling agent;

(c) the mitochondrial uncoupling agent, the ATP synthase inhibitor, the ETC inhibitor;

(d) the mitochondrial uncoupling agent, the ETC inhibitor, the ATP synthase inhibitor;

(e) the ETC inhibitor, the ATP synthase inhibitor, the mitochondrial uncoupling agent; or (f) the ETC inhibitor, the mitochondrial uncoupling agent, the ATP synthase inhibitor.

5. The method of claim 1, wherein:

(i) the ATP synthase inhibitor, the mitochondrial uncoupling agent, and the ETC inhibitor are contacted with the cell sample in the order of (from first to last): the ATP synthase inhibitor, the mitochondrial uncoupling agent, the ETC inhibitor;

(ii) contacting the cell sample with the ATP synthase inhibitor, the mitochondrial uncoupling agent, and the ETC inhibitor occurs within 10 hours (e.g., within 1, 2, 3, 4, 5, 6, 7, 8, or 9 hours, within 1, 2, 5, 10, 15, 30, 45, 60, 80, or 90 minutes, within 1, 2, 5, 10, 15, 30, 45, or 60 seconds, or within 1, 10, 50, 100, 200, 400, 600, or 800 milliseconds) of one another;

(iii) contacting the cell sample with the ATP synthase inhibitor, the mitochondrial uncoupling agent, and the ETC inhibitor occurs within a time period suitable for rapid instrument data acquisition, e.g., within 1, 10, 50, 100, 200, 400, 600, or 800 milliseconds;

(iv) contacting the cell sample with the ATP synthase inhibitor, the mitochondrial uncoupling agent, and the ETC inhibitor occurs within a time period suitable for a long-term end-point measurement, e.g., within 1, 2, 3, 4, 5, 6, 7, 8, or 9 hours;

(v) the ATP synthase inhibitor comprises oligomycin A;

(vi) the ATP synthase inhibitor (e.g., oligomycin A) is present at a concentration of at least 1 nM up to the solubility limit of the ATP synthase inhibitor (e.g., oligomycin A), e.g., 1 nM to 100 mM, 10 nM to 10 mM, 0.1 μM to 1 mM, 0.1 μM to 100 μM, 0.1 μM to 10 μM, 0.2 μM to 5 μM, 0.5 μM to 2 μM, 0.2 μM to 4 μM, 0.2 μM to 3 μM, 0.2 μM to 1 μM, 0.2 μM to 0.5 μM, 4 μM to 5 μM, 3 μM to 5 μM, 2 μM to 5 μM, 1 μM to 5 PM, 0.5 μM to 5 μM, 1 μM to 3 μM, 2 μM to 4 μM, 1 μM to 2 μM, 0.5 μM to 2.5 μM, e.g., 0.2 μM, 0.5 μM, 1 μM, 1.5 μM, 2 μM, 2.5 μM, 3 μM, 3.5 μM, 4 μM, 4.5 μM, or 5 μM, in the reaction mixture, optionally wherein the ATP synthase inhibitor (e.g., oligomycin A) is present at a concentration of 1 μM to 2 μM, e.g., 1.5 μM, in the reaction mixture;

(vii) the mitochondrial uncoupling agent comprises BAM15;

(viii) the mitochondrial uncoupling agent (e.g., BAM15) is present at a concentration of at least 1 nM up to the solubility limit of the mitochondrial uncoupling agent (e.g., BAM15), e.g., 1 nM to 100 mM, 10 nM to 10 mM, 0.1 μM to 1 mM, 0.1 μM to 100 μM, 0.1 μM to 10 μM, 0.5 μM to 10 μM, 1 μM to 8 μM, 2 μM to 6 μM, 3 μM to 4 μM, 0.5 μM to 8 μM, 0.5 μM to 6 μM, 0.5 μM to 4 μM, 0.5 μM to 2 μM, 0.5 μM to 1 μM, 8 μM to 10 μM, 6 μM to 10 μM, 4 μM to 10 μM, 2 μM to 10 μM, 1 μM to 10 μM, 1 μM to 3 μM, 2 μM to 4 μM, 3 μM to 5 μM, 4 μM to 6 μM, 5 μM to 7 μM, 6 μM to 8 μM, 7 μM to 9 μM, 2 μM to 3 μM, 1 μM to 4 μM, e.g., 0.5 μM, 1 μM, 1.5 μM, 2 μM, 2.5 μM, 3 μM, 3.5 μM, 4 μM, 5 μM, 6 μM, 7 μM, 8 μM, 9 μM, or 10 μM, in the reaction mixture, optionally wherein the mitochondrial uncoupling agent (e.g., BAM15) is present at a concentration of 2 μM to 3 μM, e.g., 2.5 μM, in the reaction mixture;

(ix) the ETC inhibitor comprises rotenone, antimycin A, or a combination thereof, optionally wherein the ETC inhibitor comprises rotenone and antimycin A;

(x) the ETC inhibitor (e.g., rotenone, antimycin A, or a combination thereof) is present at a concentration of at least 1 nM up to the solubility limit of the ETC inhibitor (e.g., rotenone, antimycin A, or a combination thereof), e.g., 1 nM to 100 mM, 10 nM to 10 mM, 0.1 μM to 1 mM, 0.1 μM to 100 μM, 0.1 μM to 10 μM, 0.1 μM to 5 μM, 0.2 μM to 2 μM, 0.5 μM to 1 μM, 0.1 μM to 4 μM, 0.1 μM to 3 μM, 0.1 μM to 2 μM, 0.1 μM to 1 μM, 0.1 μM to 0.5 μM, 4 μM to 5 μM, 3 μM to 5 μM, 2 μM to 5 μM, 1 μM to 5 μM, 0.5 μM to 5 μM, 0.2 μM to 1 μM, 0.5 μM to 2 μM, 0.2 μM to 1 μM, e.g., 0.1 μM, 0.2 μM, 0.3 μM, 0.4 μM, 0.5 μM, 0.6 μM, 0.7 μM, 0.8 μM, 0.9 μM, 1 μM, 1.5 μM, 2 μM, 2.5 μM, 3 μM, 4 μM, or 5 μM, in the reaction mixture, optionally wherein the ETC inhibitor comprises rotenone at a concentration of 0.2 μM to 1 μM (e.g., 0.5 μM) and antimycin A at a concentration of 0.2 μM to 1 μM (e.g., 0.5 μM), in the reaction mixture;

(xi) forming the reaction mixture further comprises contacting the cell sample with an agent that induces an increase in energetic demand, e.g., an ionophore (e.g., monensin), optionally wherein:
   (a) the ionophore (e.g., monesin) is present at a concentration of at least 1 nM up to the solubility limit of the ionophore (e.g., monesin), e.g., 1 nM to 100 mM, 10 nM to 10 mM, 0.1 μM to 1 mM, 1 μM to 100 μM, 5 μM to 100 μM, 10 μM to 80 μM, 20 μM to 60 μM, 30 μM to 50 μM, 5 μM to 80 μM, 5 μM to 60 μM, 5 μM to 40 μM, 5 μM to 20 μM, 5 μM to 10 μM, 80 μM to 100 μM, 60 μM to 100 μM, 40 μM to 100 μM, 20 μM to 100 μM, 10 μM to 100 μM, 10 μM to 40 μM, 20 μM to 60 μM, 40 μM to 80 μM, 15 μM to 25 μM, or 10 μM to 30 μM, e.g., 5 μM, 10 μM, 20 μM, 30 μM, 40 μM, 50 μM, 60 μM, 70 μM, 80 μM, 90 μM, or 100 μM, in the reaction mixture, optionally wherein the ionophore (e.g., monesin) is present at a concentration of 10 μM to 30 μM, e.g., 20 μM, in the reaction mixture, and/or
   (b) wherein the ionophore (e.g., monesin) is prepared as a stock solution at a concentration of 200 μM to 300 μM (e.g., 240 μM) in EtOH 10% in assay media;

(xii) the $VOC_{Mix}$ comprises a value for oxygen consumption for the reaction mixture, e.g., a value based on a measurement of oxygen consumption for the reaction mixture made after formation of the reaction mixture, optionally wherein:
   (a) the oxygen consumption is measured (e.g., directly or indirectly) by oxygen consumption rate (OCR), and/or
   (b) acquiring the $VOC_{Mix}$ comprises determining (e.g., measuring) an OCR for the reaction mixture, further optionally determining (e.g., measuring) the OCR for the reaction mixture comprises sensing a metabolite (e.g., $O_2$), e.g., consumed from medium;

(xiii) the $VPE_{Mix}$ comprises a value for proton efflux for the reaction mixture, e.g., a value based on a measurement of proton efflux for the reaction mixture after formation of the reaction mixture, optionally wherein:
   (a) the proton efflux is measured (e.g., directly or indirectly) by proton efflux rate (PER),
   (b) an extracellular acidification rate (ECAR) is measured to produce a value for proton efflux,
   (c) acquiring the PER comprises determining (e.g., measuring) a PER for the reaction mixture, further optionally wherein determining (e.g., measuring) the PER for the reaction mixture comprises sensing a cell constituent disposed in the media;

(xiv) the $VOC_{Mix}$ and the $VPE_{Mix}$ are based on measurements of oxygen consumption and proton efflux initiated within 10 hours (e.g., within 1, 2, 3, 4, 5, 6, 7, 8, or 9 hours, within 1, 2, 5, 10, 15, 30, 45, 60, 80, or 90 minutes, within 1, 2, 5, 10, 15, 30, 45, or 60 seconds, or within 1, 10, 50, 100, 200, 400, 600, or 800 milliseconds) of one another, optionally wherein:
   (a) the $VOC_{Mix}$ and the $VPE_{Mix}$ are based on measurements of oxygen consumption and proton efflux initiated within a time period suitable for rapid instrument data acquisition, e.g., within 1, 10, 50, 100, 200, 400, 600, or 800 milliseconds, or
   (b) the $VOC_{Mix}$ and the $VPE_{Mix}$ are based on measurements of oxygen consumption and proton efflux initiated within a time period suitable for a long-term end-point measurement, e.g., within 1, 2, 3, 4, 5, 6, 7, 8, or 9 hours;

(xv) the $VOC_{Mix}$ and the $VPE_{Mix}$ are based on measurements of oxygen consumption and proton efflux initiated sequentially; and/or (xvi) the $VOC_{Mix}$ and the $VPE_{Mix}$ are based on measurements of oxygen consumption and proton efflux initiated substantially simultaneously.

6. The method of claim 1, wherein two or all of the ATP synthase inhibitor, the mitochondrial uncoupling agent, and the ETC inhibitor are contacted with the cell sample simultaneously or partly simultaneously;
optionally wherein the following are contacted with the cell sample simultaneously:
   (a) the ATP synthase inhibitor, the mitochondrial uncoupling agent;
   (b) the ATP synthase inhibitor, the ETC inhibitor;
   (c) the mitochondrial uncoupling agent, the ETC inhibitor; or
   (d) the ATP synthase inhibitor, the mitochondrial uncoupling agent, the ETC inhibitor; further optionally wherein forming the reaction mixture comprises mixing any two or all of the ATP synthase inhibitor, the mitochondrial uncoupling agent, or the ETC inhibitor, prior to being contacted with the cell sample.

7. The method of claim 1, further comprising:
(i) providing the $VOC_{Ref}$, the $VPE_{Ref}$, the $VOC_{Mix}$, and the $VPE_{Mix}$ to a software program and using the software program to calculate the bioenergetic poise and bioenergetic capacity (e.g., converting to OCR and PER values) of the cell sample;
(ii) disposing the cell sample in a well or microchamber (e.g., of a multiwell plate) prior to acquiring a $VOC_{Ref}$ and a $VPE_{Ref}$,
(iii) acquiring a cell sample prior to disposing the cell sample in a well or microchamber (e.g., of a multiwell plate);
(iv) acquiring a value for glycolytic proton efflux for the reaction mixture ($VglycoPE_{Mix}$), optionally wherein the $VglycoPE_{Mix}$ is measured by glycolytic proton efflux rate (glycoPER), further optionally wherein the glycoPER is determined by mathematically removing the contribution of $CO_2$;
(v) acquiring a value for basal mitochondrial ATP production rate, optionally wherein the value for basal mitochondrial ATP production rate is acquired by subtracting the minimum oxygen consumption rate (oligo OCR) from the oxygen consumption rate (OCR) before formation of the reaction mixture (basal OCR) and multiplying by a constant, optionally wherein:

(a) the oligo OCR is the minimum OCR after the ATP inhibitor (e.g., oligomycin) is contacted with the cell sample, (b) the constant is 2.75 (called P/O Ratio)*2 (to convert oxygen atoms to oxygen molecules), and/or (c) the basal OCR is a measurement (e.g., any previous measurement, e.g., the last measurement or an average of a number of measurements), of OCR, before the first contacting (e.g., injection) of any of the ATP synthase, the uncoupling agent, or the ETC inhibitor;

(vi) acquiring a value for basal glycolytic ATP production rate, optionally wherein the value for basal glycolytic ATP production rate is acquired using the measurements of extracellular acidification rate (ECAR) before formation of the reaction mixture (e.g., before contacting the cell sample with the ATP synthase inhibitor (e.g., oligomycin A)) and converting the proton efflux rate (PER), further optionally wherein converting the PER comprises considering the buffer capacity of the medium employed in the method and the volume of the well or microchamber that holds the cell sample and discounting the contribution of extracellular $CO_2$ production, e.g., calculated from the measurements of the basal oxygen consumption rate (OCR) and the minimum measurement after contacting the cell sample with the ETC inhibitor (e.g., rotenone, antimycin, or a combination thereof) and before any following contacting step (e.g., injection), e.g., contacting the cell sample with an ionophore (e.g., monensin), additionally optionally wherein the minimum measurement is an average of the lower range after the ETC inhibitor is contacted with the cell sample;

(vii) acquiring a value for maximal respiratory capacity, optionally wherein the value for maximal respiratory capacity is acquired by using the maximal measurement of oxygen consumption rate (OCR) after contacting the cell with the uncoupling agent (e.g., BAM15) and discounting the minimum measurement of oxygen consumption rate (OCR) after contacting the cell sample with the ETC inhibitor (e.g., rotenone, antimycin, or a combination thereof) and before any following contacting step (e.g., injection), e.g., contacting the cell sample with an ionophore (e.g., monensin);

(viii) acquiring a value for reserve aerobic capacity (also known as spare respiratory capacity), optionally wherein:

(a) the value for reserve aerobic capacity is acquired by determining the difference between maximal measurement of oxygen consumption rate (OCR) after contacting the cell sample with the uncoupling agent (e.g., BAM15) and last measurement of oxygen consumption rate (OCR) before contacting the cell sample with the first of any of the ATP synthase inhibitor (e.g., oligomycin A), the uncoupling agent (e.g., BAM15), or the ETC inhibitor (e.g., rotenone, antimycin, or a combination thereof), and/or (b) the value for reserve aerobic capacity is expressed in units of ATP production rate multiplying by the factor 5.5;

(ix) acquiring a value for maximal mitochondrial bioenergetic capacity, optionally wherein the value for maximal mitochondrial bioenergetic capacity is acquired by using the maximal measurement of oxygen consumption rate (OCR) after contacting the cell sample with the uncoupling agent (e.g., BAM15) and discounting the minimum measurement after contacting the cell sample with the ATP synthase (e.g., oligomycin A) and before any following contacting (e.g., injection) step (e.g., the contacting (e.g., injection) of the ETC inhibitor) and multiplying by 5.5;

(x) acquiring a value for compensatory (or maximal glycolytic capacity), optionally wherein the value for compensatory (or maximal glycolytic capacity) is acquired using the maximal measurement of proton efflux rate (PER) after contacting the cell sample with the ETC inhibitor (e.g., rotenone, antimycin A, or a combination thereof), optionally further after contacting the cell sample with an ionophore (e.g., monensin); and/or (xi) acquiring a reference value for extracellular acidification ($VEA_{Ref}$); and acquiring a value for extracellular acidification for the reaction mixture ($VEA_{Mix}$).

8. The method of claim 1, wherein:

(i) the cell sample comprises a plurality of cells disposed in media;

(ii) the cell sample comprises immune cells, optionally wherein the immune cells are immune effector cells;

(iii) the cell sample comprises T cells (e.g., CD4+ T cells, CD8+ T cells, optionally wherein the T cells comprise T helper cells ($T_H$ cells or CD4+ T cells, e.g., Th1, Th2, Th17, Th9, or Tfh), cytotoxic T cells ($T_C$ cells or CD8+ T cells), memory T cells (e.g., central memory T cells ($T_{CM}$ cells, CD45RO+CCR7+CD62L+), effector memory T cells ($T_{EM}$ cells, $T_{EMRA}$ cells, CD45RO+ CCR7−CD62L−), tissue resident memory T cells ($T_{RM}$, CD103+), or virtual memory T cells (e.g., CD4 virtual memory T cells or CD8 virtual memory T cells)), regulatory T cells (Treg, e.g., CD4+FOXP3+Tregs or CD4+FOXP3−Tregs), innate-like T cells, natural killer T cells (NKT cells), mucosal associated invariant T cells, gamma delta T cells, or any combination thereof, (iv) the cell sample comprises engineered T cells, e.g., CAR-T cells or TCR-T cells, (v) the cell sample comprises primary T cells, e.g., primary naïve T cells (e.g., human or murine primary naïve T cells), (vi) the cell sample comprises NK cells or CD56+CD3− cells, optionally wherein:

(a) the NK cells comprise $CD56^{bright}$ NK cells, $CD56^{dim}$ NK cells, or a combination thereof, (b) the cell sample comprises engineered NK cells, e.g., CAR-NK cells or TCR-NK cells, and/or (c) the cell sample comprises CAR-NK cells, (vii) the cell sample comprises primary NK cells, e.g., primary naïve NK cells (e.g., human or murine primary naïve NK cells);

(viii) the cell sample comprises immortalized immune cells, e.g., THP1 cells;

(ix) the cell sample comprises suspension cells;

(x) the cell sample comprises cells having an average size of 15 μm or less, e.g., 14 μm or less, 13 μm or less, 12 μm or less, 11 μm or less, 10 μm or less, 9 μm or less, 8 μm or less, 7 μm or less, 6 μm or less, 5 μm or less, or 4 μm or less, in diameter, e.g., 4 μm to 12 μm, 4 μm to 10 μm, 4 μm to 8 μm, 5 μm to 7 μm, 5 μm to 6 μm, or 6 μm to 7 μm, e.g., in diameter;

(xi) the cell sample comprises cells that are suitable for a cell therapy, e.g., an adoptive cell therapy (ACT);

(xii) the cell sample comprises cells from a subject, e.g., a subject having, or is at risk of having, a disorder, e.g., a cancer or an immune disorder; and/or (xiii) the cell sample comprises at least 10, 20, 30, 40, 50, 60, 70, 80, or 90% (by number) immune cells (e.g., T cells or NK cells).

9. A method of monitoring the production of an engineered cell product, comprising evaluating the bioenergetic poise and bioenergetic capacity of a cell sample of the engineered cell product according to claim 1, thereby monitoring the production of the engineered cell product.

10. A method optimizing a cell design, comprising evaluating the bioenergetic poise and bioenergetic capacity of a cell sample having the cell design according to claim 1, thereby optimizing the cell design.

11. A method optimizing a culture medium, comprising evaluating the bioenergetic poise and bioenergetic capacity of a cell sample that has been cultured in the culture medium according to according to claim 1, thereby optimizing the culture medium.

12. A method optimizing a culture condition, comprising evaluating the bioenergetic poise and bioenergetic capacity of a cell sample that has been cultured under the culture condition according to claim 1, thereby optimizing the culture condition.

13. A method of evaluating the quality of a cell preparation, comprising evaluating the bioenergetic poise and bioenergetic capacity of a cell sample of the cell preparation according to according to claim 1, thereby evaluating the quality of the cell preparation.

14. A method of evaluating a metabolic response of a cell to a physiologically relevant condition, comprising evaluating the bioenergetic poise and bioenergetic capacity of a cell sample according to claim 1, thereby evaluating the metabolic response; wherein the physiologically relevant condition is associated with a tumor microenvironment, including reduced $O_2$, reduced/altered metabolic substrates, decreased pH, or a combination thereof.

15. A cell therapy product for use in a method of treating a disorder in a subject, wherein the method comprises evaluating the bioenergetic poise and bioenergetic capacity of a cell sample of the cell therapy product according to claim 1.

16. The method of claim 1, wherein the ATP synthase inhibitor and the ETC inhibitor are contacted with the cell sample simultaneously in a first well of a multi-well plate, wherein the ATP synthase inhibitor, the mitochondrial uncoupling agent, and the ETC inhibitor are contacted with a second cell sample in a second well of the multi-well plate simultaneously.

17. The method of claim 1, wherein the ATP synthase inhibitor and the ETC inhibitor are contacted with the cell sample simultaneously in a first well of a multi-well plate, wherein the mitochondrial uncoupling agent and the ETC inhibitor are contacted with a second cell sample in a second well of the multi-well plate simultaneously, and at a different time from when the ATP synthase inhibitor is contacted with the second cell sample, wherein:
- (i) a first value for oxygen consumption and a first value for proton efflux are acquired after the ATP synthase inhibitor is contacted with the second cell sample; and
- (ii) a second value for oxygen consumption and a second value for proton efflux are acquired after the mitochondrial uncoupling agent and the ETC inhibitor are contacted with the second cell sample.

18. The method of claim 1, wherein the ATP synthase inhibitor and the ETC inhibitor are contacted with the cell sample simultaneously in a first well of a multi-well plate, wherein the ATP synthase inhibitor and the ETC inhibitor are contacted with a second cell sample in a second well of the multi-well plate simultaneously, and at a different time from when the mitochondrial uncoupling agent is contacted with the second cell sample, wherein:
- (i) a first value for oxygen consumption and a first value for proton efflux are acquired after the ATP synthase inhibitor and the ETC inhibitor are contacted with the second cell sample; and
- (ii) a second value for oxygen consumption and a second value for proton efflux are acquired after the mitochondrial uncoupling agent is contacted with the second cell sample.

19. A method of making engineered cells, comprising:
modifying cells to express a transgene encoding a protein of interest; and
evaluating the bioenergetic poise and bioenergetic capacity of a cell sample of the engineered cells by:
- acquiring a reference value for oxygen consumption ($VOC_{Ref}$):
- acquiring a reference value for proton efflux ($VPE_{Ref}$);
- contacting the cell sample with an Adenosine Triphosphate (ATP) synthase inhibitor, a mitochondrial uncoupling agent, and an electron transport chain (ETC) inhibitor, sequentially, each contacting forming a reaction mixture, wherein:
  - (i) a first value for oxygen consumption and a first value for proton efflux are acquired after the ATP synthase inhibitor is contacted with the cell sample;
  - (ii) a second value for oxygen consumption and a second value for proton efflux are acquired after the mitochondrial uncoupling agent is contacted with the cell sample; and
  - (iii) a third value for oxygen consumption and a third value for proton efflux are acquired after the ETC inhibitor is contacted with the cell sample;
- acquiring a value for oxygen consumption for each reaction mixture ($VOC_{Mix}$);
- acquiring a value for proton efflux for each reaction mixture ($VPE_{Mix}$), thereby evaluating the bioenergetic poise and bioenergetic capacity of the cell sample, thereby making the engineered cells.

20. A method of treating a disorder in a subject, comprising:
- evaluating the bioenergetic poise and bioenergetic capacity of a cell sample of a cell therapy product according to according by:
- acquiring a reference value for oxygen consumption ($VOC_{Ref}$):
- acquiring a reference value for proton efflux ($VPE_{Ref}$):
- contacting the cell sample with an Adenosine Triphosphate (ATP) synthase inhibitor, a mitochondrial uncoupling agent, and an electron transport chain (ETC) inhibitor, sequentially, each contacting forming a reaction mixture, wherein:
  - (i) a first value for oxygen consumption and a first value for proton efflux are acquired after the ATP synthase inhibitor is contacted with the cell sample;
  - (ii) a second value for oxygen consumption and a second value for proton efflux are acquired after the mitochondrial uncoupling agent is contacted with the cell sample; and
  - (iii) a third value for oxygen consumption and a third value for proton efflux are acquired after the ETC inhibitor is contacted with the cell sample;
- acquiring a value for oxygen consumption for each reaction mixture ($VOC_{Mix}$);
- acquiring a value for proton efflux for each reaction mixture ($VPE_{Mix}$), thereby evaluating the bioenergetic poise and bioenergetic capacity of the cell sample, administering the cell therapy product to the subject, and thereby treating the disorder in the subject.

21. A system for evaluating the bioenergetic poise and bioenergetic capacity of a cell sample, comprising:

(i) a stage adapted to support a multiwell plate;

(ii) a sensor adapted to sense a metabolite, or a cell constituent, associated with the cell sample, consumed from the medium or disposed in the medium; and (iii) a dispensing system adapted to introduce fluids into the well or microchamber, wherein the stage, sensor, and dispensing system cooperate to:

acquire a reference value for oxygen consumption ($VOC_{Ref}$) and a reference value for proton efflux ($VPE_{Ref}$) for the cell sample using the sensor;

use the dispending system to contact the cell sample with an ATP synthase inhibitor, a mitochondrial uncoupling agent, and an electron transport chain (ETC) inhibitor, thereby forming a reaction mixture, wherein:

(i) a first value for oxygen consumption and a first value for proton efflux are acquired after the ATP synthase inhibitor is contacted with the cell sample;

(ii) a second value for oxygen consumption and a second value for proton efflux are acquired after the mitochondrial uncoupling agent is contacted with the cell sample; and (iii) a third value for oxygen consumption and a third value for proton efflux are acquired after the ETC inhibitor is contacted with the cell sample;

acquire a value for oxygen consumption for the reaction mixture ($VOC_{Mix}$) and a value for proton efflux for the reaction mixture ($VPE_{Mix}$) using the sensor, thereby evaluating the bioenergetic poise and bioenergetic capacity of the cell sample.

22. The system of claim 21, wherein:

(i) the dispensing system comprises at least one unit disposed above the well or microchamber;

(ii) the sensor comprises an optical sensor, optionally wherein the sensor is adapted to sense a fluorophore; and (iii) the system further comprises a computer module and software adapted to calculate the bioenergetic poise and bioenergetic capacity based on information communicated to the computer module by the sensor.

* * * * *